United States Patent [19]

Itoh et al.

[11] Patent Number: 4,835,312

[45] Date of Patent: May 30, 1989

[54] PRODUCTION PROCESS OF N-SUBSTITUTED AMIDE COMPOUNDS

[75] Inventors: Hiroshi Itoh, Yokohama; Toshimi Nakagawa, Fujisawa; Atsuhiko Nitta, Yokohama, all of Japan

[73] Assignee: 501 Mitsui Chemicals, Incorporated, Tokyo, Japan

[21] Appl. No.: 881,087

[22] Filed: Jul. 2, 1986

Related U.S. Application Data

[63] Continuation-in-part of Ser. No. 556,563, Nov. 30, 1983, abandoned.

[51] Int. Cl.$^4$ ............................................. C07C 103/133
[52] U.S. Cl. ..................................... 564/205; 564/207
[58] Field of Search ............... 564/204, 205, 142, 207, 564/143, 80

[56] References Cited

U.S. PATENT DOCUMENTS

| | | | |
|---|---|---|---|
| 3,057,861 | 10/1962 | Florey et al. | 564/142 X |
| 3,242,213 | 3/1966 | Raleigh et al. | 564/142 X |
| 3,833,597 | 9/1974 | Hardy et al. | 564/143 X |
| 3,852,350 | 12/1974 | Wilson, Jr. et al. | 564/142 X |
| 4,008,066 | 2/1977 | Moser | 564/143 X |
| 4,113,774 | 9/1978 | Surrey et al. | 564/142 X |
| 4,288,592 | 9/1981 | Rauhut et al. | 564/143 X |

OTHER PUBLICATIONS

Johnstone et al., "Tetrahedron", vol. 35, pp. 2169–2173 (1979).

*Primary Examiner*—Robert V. Hines
*Attorney, Agent, or Firm*—Schmeiser, Morelle & Watts

[57] ABSTRACT

An N-substituted amide compound is produced with a high yield by initiating a reaction among a starting amide compound such as a saturated or unsaturated, aliphatic or aromatic carboxylic acid amide, a halogen-substituted compound such as an alkyl halide and a strongly basic substance while maintaining the basic substance in a suspended state.

1 Claim, No Drawings

PRODUCTION PROCESS OF N-SUBSTITUTED AMIDE COMPOUNDS

This application is a continuation-in-part of application Ser. No. 556,563, filed Nov. 30, 1983 and now abandoned.

BACKGROUND OF THE INVENTION (a) Field of the Invention

This invention relates to an improved production process of N-monosubstituted amide compounds. It also relates to a novel production process of N,N-disubstituted amide compounds.

(b) Description of the Prior Art

Since N-substituted amide compounds generally contain well-balanced hydrophilic groups and hydrophobic groups in their molecules, they have such advantages that their miscibility with various substances are good, they exhibit strong resistance to hydrolysis, and unsaturated amide compounds pertain excellent homopolymerization or copolymerization property. Owing to such advantages, a wide variety of application fields are known for N-substituted amine compounds, including adhesive, paint, paper-processing agents, textile-processing agents, emulsion, urethane stiffeners, pigment dispersants, plastics additives, polymeric coagulants, ion-exchange resins, etc. They are also useful as starting materials or intermediates for or even final products of compounds having a complex structure such as pharmaceutical products, agricultural chemicals, amino acids, naturally-occurring substances, etc. and, also, as a starting material for the production of amines. Notwithstanding such advantages and usefulness of N-substituted amide compounds, they have not yet been used in a great quantity as no inexpensive industrial production process has yet been established for N-substituted amide compounds.

As known industrial production processes of N-substituted amide compounds, may be mentioned a production process relying upon the reaction between a carboxylic chloride and an amine as well as another production process which makes use of the Ritter reaction. However, under the current circumstances, N-substituted amide compounds produced in accordance with such conventional processes are either expensive or are limited to certain specific types, thereby limiting their applications to specific fields.

Furthermore, as a general production process of N-substituted amide compounds, there has been known to convert an amide compound to an amide compound substituted by one or more alkali metals under the influence of a strongly basic substance such as alkali metal alkoxide and then to convert the thus-alkali metal substituted amide compound to an N-substituted amide compound under the influence of a halogen-substituted compound such as alkyl halide. Reference may, for example, be made to Hikkinbottom, W. J., *Reactions of Organic Compounds* (Vol. 3), Longmans, Green and Co., (1957) and U.S. Pat. No. 3,084,191. However, this process involves varied inconvenience such that the process comprises two steps; it requires as a reaction solvent a protonic solvent having high reactivity in the presence of a basic catalyst with a halogen-substituted compound, such as liquid ammonia or an alcohol; it also requires an extremely strong basic substance which is irksome to handle, such as an alkali metal amide, alkali metal hydride, or alkali metal alkoxide. Due to such inconvenience, as shown in Comparative Examples 1 through 3 which will be described later, this process involves such problems that the yield of an intended final product is low, the halogen-substituted compounds reactable with the alkali metal substituted amide compound are limited to specific ones and the reaction product is exclusively an N-monosubstituted amide compound and, where an N,N-disubstituted amide compound is intended, the process has to be repeated similarly. For the reasons mentioned above, this process has not been adopted in an industrial large scale as a production process for general N-substituted amide compounds.

Alternatively, as disclosed on Page 266 of G. L. Isele, A. Lüttringhous, Synthesis 1971 (5), it has been known to use a two-step production process in which, after reacting an amide compound with a strongly basic substance in an aprotic polar solvent to form an alkali metal-substituted amide compound, the alkali metal-substituted amide compound is reacted with a halogen-substituted compound such as an alkyl halide to obtain an N-alkyl-substituted-amide compound. However, even if this process was followed, no satisfactory results have been obtained as described in Comparative Example 2.

In addition, USSR Certificate of Inventorship No. 667,547 discloses a production process of N-alkylated organic compounds, in which a basic substance such as caustic soda is added in the form of an aqueous solution and the substitution reaction is initiated while keeping all the basic substance in a liquid state. According to the disclosure of the certificate, it is mentioned that, in the above process, the presence of water in the reaction mixture is extremely convenient for the proceeding of the reaction. According to a study made by the present inventors, as will be apparent from a comparison between Examples 1, 3 and 4 and Comparative Example 4 which will also be described later, this process is accompanied by a considerable occurrence of reaction by-products, whereby making its selectivity of an intended N-substituted amide compound poor and, depending on an N-substituted amide compound intended, resulting in a considerable reduction of its yield.

In the case where the starting amide compound, to which the present invention is directed, is an unsaturated compound, N,N-substitution reaction does not take place in the same manner as in the case of the saturated compounds disclosed in Johnstone et al., Tetrahedron, Vol. 35, pages 2169–2173. In this regard, the general alkylation procedure recited on page 2173, left column, of the Johnstone et al. reference, shows an example of the use of potassium hydroxide in an amount of 4 m moles per replaceable hydrogen of substrate, i.e., 8 moles per one mole of the substrate. However, in the case where such a large amount of potassium is used in an N-substitution reaction of unsaturated compounds, polymerization and other side reactions take place.

SUMMARY OF THE INVENTION

An object of this invention is to provide a production process, which can produce not only an N-monosubstituted amide compound but also an N,N-disubstituted amide compound in a single-step reaction.

Another object of this invention is to provide a production process, which is substantially free of side reactions and can thus produce an intended N-substituted amide compound with good selectivity.

A further object of this invention is to provide a production process, which is suitable for the production of a wide variety of N-substituted amide compounds.

According to a process of this invention, a wide variety of N-monosubstituted amide compounds and N,N-disubstituted amide compounds can each be produced with a high yield without substantially causing side reactions to occur by bringing a strongly basic substance, a starting amide compound and a halogen-substituted compound into a simultaneous contact in a reaction system containing an aprotic polar solvent to initiate a reaction while maintaining the strongly basic substance in a suspended state.

DETAILED DESCRIPTION OF THE INVENTION

The process according to this invention features very little occurrence of side reactions and thus a high yield of an intended product. It is capable of producing a wide variety of N-substituted amide compounds as it permits reactions between an extremely wide range of amide compounds and an extremely broad variety of halogen-substituted compounds by combining them suitably. Moreover, it enables to produce each of N-monosubstituted amide compounds and N,N-disubstituted amide compounds in a single-step reaction by selecting suitable production conditions. It is also possible to produce an N,N-disubstituted amide compound having different substituent groups. The above successful process of the present invention is based on the present inventors' finding that the presence of water in the reaction system, which has heretofore been considered to be convenient, serves to induce side reactions contrary to what has been believed and impedes the production of an intended N-substituted amide compound; and, instead of reacting an amide compound and a strongly basic substance first and then causing a halogen-substituted compound to react with a reaction product of the amide product and basic substance as proposed by the prior art, it is necessary to bring the strongly basic substance, amide compound and halogen-substituted compound into a simultaneous contact to react them together.

Accordingly, either one of the following processes may be suitably selected in the present invention:

(a) The three starting materials are simultaneously added to and mixed in an aprotic polar solvent and the strongly basic substance is suspended therein to react them together;

(b) The strongly basic substance is suspended in an aprotic polar solvent and the amide compound and halogen-substituted compound are then simultaneously supplied into the suspension to react them together; and (c) The amide compound and halogen-substituted compound are dissolved or suspended in an aprotic polar solvent and the strongly basic substance is then added and suspended.

Amide compounds, to which the present invention is directed, may be roughly divided into two groups, one being monoamide compounds and the other polyamide compounds higher than diamide compounds.

As monoamide compounds, may be mentioned saturated aliphatic carboxylic amides, unsaturated aliphatic carboxylic amides, aromatic carboxylic amides, alicyclic carboxylic amides as well as urea and its derivatives. Saturated aliphatic carboxylic amides are represented by a general formula $C_nH_{2n+1}CONH_2$ in which n is an integer of 0–20. Also included are those containing at least one of at least one type of substituent groups such as nitro, cyano, amino, carboxyl, sulfo, alkoxy and carboxylic acid ester groups. Unsaturated aliphatic carboxylic acid amides are represented by a general formula $C_nH_{2n+1-2m}CONH_2$, in which n and m stand respectively for integers of 2–20 and 1–5. These amides contain at least one carbon-to-carbon double or triple bond in their molecules. Also included are those containing at least one of at least one type of substituent groups such as nitro, cyano, amino, carboxyl, sulfo, alkoxy and carboxylic acid ester groups. Aromatic carboxylic acid amides contain in their molecules an aromatic ring. As the aromatic ring, may be mentioned a benzene, naphthalene or anthracene ring or the like. Also included are those containing at least one of at least one type of substituent groups such as nitro, cyano, alkoxy, amino, carboxyl, sulfo, carboxylic acid ester, alkyl, alkenyl and aryl groups, which substituent groups are attached to the aromatic ring. Also included are aromatic carboxylic acid amides in which one or more of the above substituent groups or aromatic ring is each attached to another aromatic ring through oxygen, sulfonyl group, sulfur or the like. Alicyclic carboxylic acid amides are those containing in their molecules an alicyclic structure and also include heterocyclic compounds formed of different elements. Urea and its derivatives are those containing an N—CO—N or N—CO—N—N atomic group, as led by urea.

Examples of the above-described monoamide compounds are, as saturated aliphatic carboxylic amides, formamide, acetamide, propionamide, butylamide, valeramide, isovaleramide, pivalamide, lauramide, myristamide, palmitamide, stearamide, methoxyacetamide, ethoxyacetamide, methoxypropionamide, ethoxypropionamide, cyanovaleramide, nitropropionamide, aminopropionamide, carbamoyl propane sulfonic acid, carbamoyl propanoic acid, methyl carbamoyl propanate, etc.

Exemplary unsaturated aliphatic carboxylic acid amides include acrylamide, methacrylamide, vinylacetamide, crotonamide, decenamide, nonadecenamide, propionamide, butynamide, hexadiene carboxamide, pentinamide, heptinamide, ethoxyacrylamide, ethoxymethacrylamide, cyanobutenamide, nitrobutenamide, aminobutynamide, carbamoyl propene sulfonic acid, carbamoyl crotonic acid, methyl carbamoyl crotonate, etc.

Among the aromatic carboxylic acid amides, there are included for example benzamide, naphthamide, anthracene carboxamide, anthraquinone carboxamide, biphenylcarboxamide, phenylacetamide, phenylpropionamide, phenyldecanamide, nitrobenzamide, nitronaphthamide, nitrocinnamide, cyanobenzamide, methoxybenzamide, ethoxybenzamide, methoxynaphthamide, N,N-dimethylaminobenzamide, N,N-dimethylaminonaphthamide, carbamoyl benzene sulfonic acid carbamoyl benzene sulfonic acid, carbamoyl naphthalene sulfonic acid, toluamide, propylbenzamide, decylbenzamide, carbamoyl naphthoic acid, vinylbenzamide, allylbenzamide, butenylbenzamide, phenylcarbamoyl phenyl ether, vinylcarbamoyl phenyl ether and phenylcarbamoyl phenyl sulfide.

As alicyclic carboxylic acid amides, may be mentioned for example cyclopropane carboxamide, cyclobutane carboxamide, cyclopentane carboxamide, cyclopentene carboxamid cyclohexane carboxamide, cycloheptane carboxamide, cyclooctane carboxamide, cyclooctene carboxamide, pyrrole carboxamide, furan carboxamide, thiophene carboxamide, cyclohexylacetamide, cyclohexylpropionamide, pyridine carboxamide, pyrrolidine carboxamide, morpholine carboxamide, imidazole carboxamide, quinoline carboxamide, etc. Examples of urea and its derivatives include, for example, urea, biuret, thiobiuret, triuret, semi-carbazide, carbonohydrazide, and carbazone.

Among these amide compounds exemplified above, unsubstituted amide compounds are preferred in permitting a reaction to proceed efficiently. As another preferred types of compounds, there may be used conjugated amide compounds in which an amido group is conjugated with a double bond, for example, unsaturated aliphatic amide compounds such as acrylamide, methacrylamide and crotonamide; and aromatic amide compounds such as benzamide, tolylamide, isopropylbenzamide and naphthamide.

On the other hand, polyamide compounds include saturated aliphathic polycarboxylic acid amides, unsaturated aliphatic polycarboxylic aid amides, aromatic polycarboxylic acid amides and alicyclic polycarboxylic acid amides.

Saturated aliphatic polycarboxylic acid amides are represented by a general formula $C_nH_{2n-m+2}(CONH_2)_m$, in which n and m are each an integer and are respectively 0-20 and 2-4. Also included are those containing at least one of at least one type of substituent groups such as nitro, cyano, amino, carboxyl, sulfo, alkoxy and carboxylic acid ester groups.

Unsaturated aliphatic polycarboxylic acid amides are represented by a general formula $C_nH_{2n+2-m-2r}(CONH_2)_m$, in which n, m and r denote individually an integer and are respectively 2-20, 2-4 and 1-4. Also included are those containing at least one of at least one type of substituent groups such as nitro, cyano, amino, carboxyl, sulfo, alkoxy and carboxylic acid ester groups.

Aromatic polycarboxylic acid amides contain in their molecules an aromatic ring, which is for example a benzene, naphthalene or anthracene ring or the like. They may be substituted by 2-6 substituent groups. Also included are those containing at least one of at least one type of substituent groups such as nitro, cyano, amino, carboxyl, sulfo, alkoxy, carboxylic acid ester, alkyl, alkenyl and aryl groups, which substituent groups are attached to an aromatic ring. Also included are those containing one or more of such substituent groups or aromatic ring each coupled with another aromatic ring through oxygen, sulfonyl sulfur or the like.

Alicyclic polycarboxylic acid amides contain an alicyclic structure in their molecules and may include heterocyclic compounds formed of different elements. They may be substituted by 2-5 substituent groups.

Certain specific examples of such polycarboxylic acid amide compounds will next be described. As saturated aliphatic carboxylic acid amides, may be mentioned for example oxalamide, malonamide, succinamide, glutaramide, adipamide, pimelamide, suberamide, azelamide, sebacamide, carbamoylmethyl methylglutaramide, butane tetracarboxamide, tetradecane dicarboxamide, methoxy adipamide, cyanoadipamide, nitroadipamide, aminoadipamide, dicarbamoyl butane sulfonic acid, dicarbamoyl butanoic acid and dicarbamoyl butylacetate.

Exemplary unsaturated aliphatic polycarboxylic acid amides include maleamide, fumaramide, citraconamide, methaconamide, decene dicarboxamide, tetradecene dicarboxamide, octadecene dicarboxamide, butene tetracarboxamide, hexadiene dicarboxamide, pentyne dicarboxamide, methoxy butene dicarboxamide, cyanobutene dicarboxamide nitrobutene dicarboxamide, amonbutene dicarboxamide, dicarbamoylbutene sulfonic acid, dicarbamoylbutenoic acid, methyl dicarbamoylbutenoate, etc.

Aromatic polycarboxylic acid amides are, for example, phthalamide, isophthalamide, terephthalamide, naphthalene dicarboxamide, anthracene dicarboxamide, anthraquinone dicarboxamide, biphenyl dicarboxamide, phenyl citraconamide, naphthalene tricarboxamide, pyromellitamide, nitrophthalide, cyanophthalide, aminophthalide, methoxyphthalide, N,N-dimethylaminophthalide, dicarbamoyl benzene sulfonic acid, dicarbamoyl benzoic acid, dicarbamoyl benzylacetate, methylphthalamide, propylphthalamide, allylphthalamide, phenyldicarbamoyl phenylether, vinyldicarbamoyl phenylether, phenyldicarbamoyl phenylsulfon, phenyldicarbamoyl phenylsulfide, etc.

As exemplary aliphatic polycarboxylic acid amides, may be mentioned cyclopropane dicarboxamide, cyclopentane dicarboxamide, camphoramide, cyclohexane dicarboxamide, cyclohexene dicarboxamide, pyrone dicarboxamide, pyridine dicarboxamide and pyridine tricarboxamide.

Among these amide compounds exemplified above, unsubstituted amide compounds are preferred in that they allow reactions to proceed efficiently. As another types of preferred compounds, there may be used conjugated amide compounds in which an amido group is conjugated with a double bond, for example, unsaturated aliphatic polyamides such as fumaramide, maleamide, and citraconamide; and aromatic polyamide compounds such as phthalamide, isophthalamide, terephthalamide and benzene tricarboxamide.

As a halogen-substituted compound to be reacted with a starting amide compound, a wide variety of compounds may be mentioned, including for example alkyl halides, alkyl polyhalides, halogenated alicyclic compounds, aryl halides, alkylaryl halides, alkenyl halides, alkenylaryl halides, carboxylic halides, sulfonic halides, halogen-substituted carboxylic acids and their esters, halogen-substituted ethers, heterocycle-containing halides and heteroatom-containing halides.

Alkyl halides are represented by a general formula $C_nH_{2n+1}X$, in which X denotes a halogen atom and n is an integer of 1-20. Alkyl polyhalides are represented by a general formula $C_nH_{2n+2-m}X_m$, in which X means a halogen atom and n and m are respectively integers of 1-20 and 2-4. Halogenated alicyclic compounds are those having in their molecules an alicyclic structure and substituted by at least one halogen atom. Their rings are each formed of 3-8 carbon atoms. Aryl halides have an aromatic ring substituted by at least one halogen atom. The aromatic ring may include benzene ring, naphthalene ring or anthracene ring. Also included are those containing at least one of at least one type of substituent groups such as alkyl, alkenyl, aryl, nitro, cyano, amino, carboxyl, sulfo, alkoxy and carboxylic acid ester groups, which substituent groups are attached to an aromatic ring. Also included are those containing one or more of the above substituent groups or aromatic ring each coupled with another aromatic ring through oxygen, sulfonyl group, sulfur or the like.

Alkenyl halides are unsaturated halogen-substituted compounds represented by a general formula $C_nH_{2n+2-m-2r}X_m$, in which X means a halogen atom and n, m and r are all integers and stand respectively for 2–10, 1–4 and 1–4.

Alkenylaryl halides are represented by a general formula $Ar_m \cdot C_nH_{2n+2-2s-m-r}X_r$, in which X and Ar denote respectively a halogen atom and an aromatic ring and n, m, r and s are all integers and stand respectively for 2–20, 1–4, 1–4 and 1–4. Here, as the aromatic ring, a benzene, naphthalene or anthracene ring may be employed. Also included are those containing at least one of at least one type of substituent groups such as alkyl, alkenyl, aryl, nitro, cyano, amino, carboxyl, sulfo, alkoxy and carboxylic acid ester groups and halogen atoms, such substituent groups and/or atoms being attached to the aromatic ring as well as those containing one or more of such substituent groups and/or atoms or aromatic ring each coupled with another aromatic ring through oxygen, sulfonyl group, sulfur or the like.

Carboxylic halides may be divided into aliphatic carboxylic halides, aromatic carboxylic halides and alicyclic carboxylic halides. Aliphatic carboxylic halides may be divided further into saturated aliphatic carboxylic halides and unsaturated aliphatic carboxylic halides.

Aliphatic carboxylic halides are represented by a general formula $C_nH_{2n+2-m-2r}(COX)_m$, in which X means a halogen atom and n, m and r are all integers and stand respectively for 2–20, at least 1 and 0–4. When $r=0$, the general formula corresponds to saturated carboxylic halides while, when $r=1-4$, the general formula corresponds to unsaturated carboxylic halides. Also included are those containing at least one of at least one type of substituent groups such as nitro, cyano, amino, carboxyl, sulfo, alkoxy and carboxylic acid ester groups.

Aromatic carboxylic halides are carboxylic halides containing in their molecules an aromatic ring. The aromatic carboxylic halides contain at least one substituent group. Here, as the aromatic ring, may be mentioned a benzene, naphthalene or anthracene ring. Also included are those containing at least one of at least one type of substituent groups such as alkyl, alkenyl, aryl, nitro, cyano, amino, carboxyl, sulfo, alkoxy and carboxylic acid ester groups, the substituent groups being attached to the aromatic ring, as well as those containing one or more of such substituent groups or aromatic ring each coupled with another aromatic ring through oxygen, sulfonyl group, sulfur or the like.

Sulfonic halides are for example aliphatic and aromatic sulfonic halides and contain at least one substituent group. Aliphatic sulfonic halides include both saturated and unsaturated aliphatic sulfonic halides, both usable in the present invention. Aromatic sulfonic halides contain as their aromatic rings a benzene, naphthalene or anthracene ring or the like. Also included are those containing at least one of at least one type of substituent groups such as alkyl, alkenyl, aryl, nitro, cyano, amino, carboxyl, sulfo, alkoxy and carboxylic acid ester groups, the substituent groups being attached to the aromatic ring, as well as those containing one or more of such substituent groups or aromatic group each coupled to another aromatic ring through oxygen, sulfonyl group, sulfur or the like.

Halogen-substituted carboxylic acids and their esters include halogen-substituted carboxylic acids, esters of halogen-substituted carboxylic acids and halogensubstituted esters of carboxylic acids. Halogen-substituted carboxylic acids are represented by a general formula $X_mC_nH_{2n+1-2r-m}(COOH)_s$, in which X represents a halogen atom, n, m and r are all integers and denote respectively 1–20, 1–4 and 0–5 and s stands for 1–4. Also included are their salts. Esters of halogen-substituted carboxylic acids are represented by a general formula $X_mC_nH_{2n+1-2r-m}(COOR)_s$, in which X means a halogen atom, n, m and r are all integers, and n, m, r and s stand respectively for 1–20, 1–4, 0–5 and 1–4. In the above formula, R is a saturated aliphatic hydrocarbon, unsaturated aliphatic hydrocarbon or aromatic hydrocarbon group. Where R represents aromatic hydrocarbon groups, the above general formula embraces those containing at least one of at least one type of substituent groups such as alkyl, alkenyl, aryl, nitro, cyano, amine, carboxyl, sulfo, alkoxy and carboxylic acid ester groups, which substituent groups are attached to an aromatic ring, as well as those containing one or more of such substituent groups or aromatic ring each coupled with another aromatic ring through oxygen, sulfonyl group, sulfur or the like. These substituent groups may be the same or different. Halogen-substituted esters of carboxylic acids are divided into esters of saturated aliphatic carboxylic acids, esters of unsaturated aliphatic carboxylic acids and esters of aromatic carboxylic acids. Esters of saturated aliphatic carboxylic acids are represented by a general formula $C_nH_{2n+1}COORX_m$, in which X is a halogen atom, n and m are each an integer and stand respectively for 0–20 and 1–4, and R represents a saturated aliphatic hydrocarbon group, unsaturated aliphatic hydrocarbon group or aromatic hydrocarbon group. Also included in this category are those containing at least one of at least one type of substituent groups such as alkyl, alkenyl, aryl, nitro, cyano, amino, carboxyl, sulfo, alkoxy and carboxylic acid ester groups, which substituent groups are attached to an aromatic ring, as well as those containing one or more of such substituent groups or aromatic ring each coupled with another aromatic ring through oxygen, sulfonyl group, sulfur or the like. Esters of unsaturated aliphatic carboxylic acids are represented by a general formula $C_nH_{2n+1-2r}COORX_m$, in which X means a halogen atom, n, m and r are all integers and stand respectively for 2–20, 1–4 and 1–4. R denotes a saturated aliphatic hydrocarbon, unsaturated aliphatic hydrocarbon or aromatic hydrocarbon group. Also included are those containing at least one of at least one type of substituent groups such as alkyl, alkenyl, aryl, nitro, cyano, amino, carboxyl, sulfo, alkoxy and carboxylic acid ester groups, the substituent groups being attached to an aromatic ring, as well as those containing one or more of such substituent groups or aromatic ring each coupled with another aromatic ring through oxygen, sulfonyl group, sulfur or the like. Esters of aromatic carboxylic acids are represented by a general formula $Ar \cdot COORX_m$, in which X means a halogen atom and m is an integer of 1–4 and Ar denotes a hydrocarbon group containing an aromatic ring. Also included are those containing at least one of at least one type of substituent groups such as alkyl, alkenyl, aryl, nitro, cyano, amino, carboxyl, sulfo, alkoxy and carboxylic acid ester groups, the substituent groups being attached to the aromatic ring, as well as those containing one or more of such substituent groups or aromatic ring each coupled with another aromatic ring through oxygen, sulfonic group, sulfur or the like.

Halogen-substituted ethers mean ethers substituted by at least one halogen atom. They may be roughly divided into aliphatic ethers and aromatic ethers. Halogen-substituted aliphatic ethers consist of saturated aliphatic ethers and unsaturated aliphatic ethers. In an unsaturated aliphatic ether, there are two types of ethers, one having one or more halogen atoms attached to a saturated hydrocarbon group and the other having one or more halogen atoms attached to an unsaturated hydrocarbon group. Aromatic ethers are also divided into two groups, one being a combination of an aliphatic residue and an aromatic residue and the other being a combination of aromatic residues. Furthermore, they may also be divided into those having one or more halogen atoms attached to an aliphatic moiety and those having one or more halogen atoms attached to an aromatic moiety. Also included are those containing at least one of at least one type of substituent groups such as alkyl, alkenyl, aryl, nitro, cyano, amino, carboxyl, sulfo, alkoxy and carboxylic acid ester groups, the substituent groups being attached to an aromatic ring, as well as those containing one or more of such substituent groups or aromatic ring each coupled with another aromatic ring through oxygen, sulfonyl group, sulfur or the like.

Heterocycle-containing halides are halides of compounds containing a heterocycle in their molecules. They contain at least one halogen atom as a substituent. There are two types of heterocycle-containing halides, one having one or more halogen atoms attached to a heterocycle and the other containing one or more halogen atoms as a haloalkyl, haloalkenyl or carboxylic halide group, which is attached to a heterocycle. Depending on the heteroatom making up each heterocycle, they may be divided into those containing an oxygen atom as the heteroatom, those having a nitrogen atom as the heteroatom and those containing a sulfur atom as the heteroatom. In addition, where two or more heteroatoms are contained to make up a heterocycle, they may be the same or different.

Heteroatom-containing halides are represented by a general formula X-R-Y, in which X denotes a halogen atom, R means an alkylene, alkenylene or like group, and Y is a substituent group containing one or more heteroatoms, such as cyano, nitro, amino, sulfo, sulfido, or sulfonyl group. Also included in the present invention are those substituted by two or more halogen atoms and those containing two or more of at least one type of the above substituent groups containing one or more heteroatoms.

Although each of chlorine-substituted bromine-substituted and iodine-substituted compounds are encompassed by the present invention, following chlorine-substituted compounds are given as representative examples of halogen-substituted compounds. Where two or more halogen atoms are incorporated, it is not necessary that such substituent halogen atoms be the same. They may be combinations of chlorine(s)-bromine(s), chlorine(s)-iodine(s) and bromine(s)-iodine(s). However, in the following specific examples of halogen-substituted compounds, substituent halogen atoms are limited to substituent chlorine atoms only.

As alkyl halides, may be mentioned for example chloromethane, chloroethane, chloropropane, chlorobutane, chloropentane, chlorohexane, chloroheptane, chlorodecane, chlorododecane, chlorotetradecane, and chlorooctadecane. Among alkyl polyhalides, there are for example dichloromethane, chloroform, tetrachloromethane, dichloroethane, trichloroethane, tetrachloroethane, dichloropropane, trichloropropane, dichlorobutane, dichloroheptane, dichlorohexane and dichlorodecane.

Halogenated alicyclic compounds include for example chlorocyclobutane, chlorocyclopentane, chlorocyclohexane, chlorocycloheptane, chlorocyclooctane, dichlorocyclooctane, chlorocyclopentene, chloromethylcyclohexane, and chloroethylcyclohexane.

Among aryl halides, may be mentioned for example benzylchloride, bezylidenedichloride, phenethylchloride, phenylpropylchloride, chloromethylnaphthalene, chloromethylanthracene, diphenylmethylchloride, triphenylmethylchloride, chloromethyltoluene, chloromethylethylbenzene, chloromethylxylene, chloromethylstyrene, nitrobenzylchloride, chloromethylanisole, chloromethylbenzoic acid, methyl chloromethylbenzoate, ethyl chloromethylbenzoate, phenyl chloromethylbenzoate, chloromethylbenzonitrile, chloromethylaniline, chloromethyl benzenesulfonic acid, chloromethylbiphenyl, chlorobenzylchloride, chloromethylphenyl phenyl ether, chloromethylphenyl phenyl sulfon and chloromethylphenyl phenyl sulfido.

As alkenyl halides, may be mentioned for example vinylchloride, vinylidenechloride, allylchloride, chloroallylchloride, propargyl chloride, methallyl chloride, chloromethallyl chloride, pentenyl chloride, hexene dichloride and octenyl chloride.

Alkenylaryl halides include for example styryl chloride, cinnamyl chloride, naphthylpropenyl chloride, anthrylpropenyl chloride, phenanthrylpropenyl chloride, ethylstyryl chloride, chlorovinyl styrene, nitrostyryl chloride, cyanostyryl chloride, chlorovinyl aniline, chlorovinyl benzoic acid, ethyl chlorovinyl benzoate, N,N-dimethylaminomethyl styrylchloride, chlorostyryl chloride, phenylstyryl chloride, methoxystyryl chloride, chlorovinylphenyl phenyl ether, chlorovinylphenyl phenyl sulfon and chlorophenyl phenyl sulfido.

Among carboxylic halides, may be mentioned for example formyl chloride, acetyl chloride, propionyl chloride, butyryl chloride, valeryl chloride, pivaloyl chloride, lauroyl chloride, myristoyl chloride, palmitoyl chloride, stearoyl chloride, oxalyl chloride, malonyl chloride, succinyl chloride, adipoyl chloride, suberoyl chloride, sebacoyl chloride, nitropropionyl chloride, cyanopropionyl chloride, aminopropionyl chloride, adipic monochloride, sulfopropionyl chloride, ethoxypropionyl chloride, methoxycarbonyl butanoic chloride, acryloyl chloride, propioloyl chloride, methacryloyl chloride, crotonoyl chloride, oleoyl chloride, maleoyl chloride, fumaroyl chloride, citraconoyl chloride, mesaconoyl chloride, decene dicarbonyl chloride, butene tetracarbonyl chloride, nitrocrotonoyl chloride, cyanocrotonoyl chloride, aminocrotonoyl chloride, maleic monochloride, sulfocrotonoyl chloride, ethoxyacryloyl chloride, methoxycarbonyl acryloyl chloride, benzoyl chloride, naphthoyl chloride, anthracene carbonyl chloride, biphenyl carbonyl chloride, phenylacetyl chloride, phenylpropionyl chloride, nitrobenzoyl chloride, nitrocinnamoyl chloride, cyanobenzoyl chloride, aminobenzoyl chloride, phthalic monochloride, acetoxybenzoyl chloride, methoxybenzoyl chloride, chloroformyl benzene sulfonic acid, toluoyl chloride, allylbenzoyl chloride, phenylchloroformyl phenyl ehter, phenylchloroformyl phenyl sulfon, phenylchloroformyl sulfido, phthaloyl chloride, cyclobutane carbonyl chloride, cyclohexane carbonyl chloride, cycloheptane carbonyl chloride, cyclooctane carbonyl chloride, cyclooctene carbonyl chloride, pyrrole carbonyl chloride, thiophene carbonyl chloride, pyridine carbonyl chloride, camphoroyl chloride, and pyridine tricarbonyl chloride.

Exemplary sulfonic acid chlorides include methane sulfonyl chloride, ethane sulfonyl chloride, propane sulfonyl chloride, hexane sulfonyl chloride, decane sulfonyl chloride, ethylene sulfonyl chloride, allylsulfonyl chloride, methallylsulfonyl chloride, crotonosulfonyl chloride, hexene sulfonyl chloride, benzene sulfonyl chloride, naphthalene sulfonyl chloride, anthracene sulfonyl chloride, anthraquinone sulfonyl chloride, tosyl chloride, biphenylsulfonyl chloride, styrene sulfonyl chloride, nitrobenzene sulfonyl chloride, dinitrobenzene sulfonyl chloride, aminobenzene sulfonyl chloride, cyanobenzene sulfonyl chloride, methoxybenzene sulfonyl chloride, chlorosulfonyl benzoic acid, chlorosulfonyl benzene sulfonic acid, methyl chlorosulfonyl benzoate, phenyl chlorosulfonyl benzoate, phenylchlorosulfonyl phenyl ether, phenyl chlorosulfonylphenyl sulfon, and phenyl chlorosulfonylphenyl sulfido.

As halogen-substituted carboxylic acids and their esters, may be mentioned for example chloroacetic acid, chloropropionic acid, chlorobutyric acid, chlorovaleric acid, chlorocaproic acid, chloroheptanoic acid, chloropalmitic acid, chlorostearic acid, chloromalonic acid, chloroacrylic acid, chloromethacrylic acid, chlorocrotonic acid, chloroleic acid, methyl chloroacetate, ethyl chloroacetate, butyl chloroacetate, hexyl chloroacetate, diethyl chloromalonate, vinyl chloroacetate, allyl chloroacetate, methallyl chloroacetate, phenyl chloroacetate, benzyl chloroacetate, phenethyl chloroacetate, phenyl chloropropionate, tolyl chloroacetate, styryl chloroacetate, nitrophenyl chloroacetate, cyanophenyl chloroacetate, chloroacetoxy benzenesulfonate, biphenyl chloroacetate, aminophenyl chloroacetate, chloroacetoxy benzoic acid, anisyl chloroacetate, diethyl chloromalonate, methyl chloroacetoxy benzoate, chloroacetoxyphenyl phenyl ether, chloroacetoxyphenyl phenyl sulfon, chloroacetoxyphenyl phenyl sulfido, chloromethyl formate, chloromethyl acetate, chloromethyl propionate, chloromethyl laurate, chloromethyl stearate, chloroethyl acetate, chlorobutyl acetate, chloropropenyl acetate, chlorobutenyl acetate, chlorophenyl acetate, chlorobenzyl acetate, chlorophenethyl acetate, chlorotolyl acetate, chlorostyryl acetate, chloronitrophenyl acetate, chlorocyanophenyl acetate, chlorosulfophenyl acetate, chloroaminophenyl acetate, acetoxy chlorobenzoic acid, anisylbiphenyl acetate, methyl acetoxy chlorobenzoate, chlorobiphenyl acetate, acetoxychlorophenyl phenyl ether, acetoxychlorophenyl phenyl sulfon, acetoxychlorophenyl phenyl sulfido, chloroethyl acrylate, chlorobutyl acrylate, chloromethyl methacrylate, chloropropenyl acrylate, chlorobutenyl methacrylate, chlorophenyl acrylate, chlorophenyl oleate, chlorobenzyl crotonate, chloronitrobenzyl crotonate, chlorocyanobenzyl methacrylate, chlorotolyl acrylate, chlorostyryl acrylate, chlorobiphenyl acrylate, acryloyloxy chlorobenzoic acid acryloyloxy benzene sulfonate, chloroanisyl acrylate, methyl acryloyloxy benzoate, acryloyloxychlorophenyl phenyl ether, acryloyloxychlorophenyl phenyl sulfon, acryloyloxychlorophenyl phenyl sulfido, chloromethyl benzoate, chlorobutyl naphthoate, chloropropenyl benzoate, chlorobutenyl naphthoate, chlorophenyl benzoate, chlorobenzyl benzoate, chlorophenyl naphthoate, chloromethoxycarbonyl toluene, chloromethoxycarbonyl styrene, chloromethoxycarbonyl biphenyl, chloromethyl nitrobenzoate, chloromethyl cyanobenzoate, chloropropenyl aminobenzoate, chloromethoxycarbonyl benzoic acid, chloropropenyl sulfobenzoate, chloromethoxycarbonylphenyl methyl ether, methyl chloromethoxycarbonyl benzoate, chloromethoxycarbonylphenyl phenyl ether, chloromethoxycarbonylphenyl phenyl sulfon, chloromethoxycarbonylphenyl phenyl sulfido, chloronitrobenzyl benzoate, chlorocyanophenyl benzoate, chloroaminophenyl benzoate, benzoyloxy chlorobenzoic acid, chlorosulfophenyl benzoate, chloroanisyl benzoate, ethyl benzoyloxy chlorobenzoate, chlorotolyl benzoate, chlorostyryl benzoate, chlorobiphenyl benzoate, benzoyloxychlorophenyl phenyl ether, benzoyloxychlorophenyl phenyl sulfon, benzoyloxychlorophenyl phenyl sulfido, chlorostyryl nitrobenzoate, and chlorosulfophenyl cyanobenzoate.

Among halogen-substituted ethers, there are for example chloromethyl methyl ether, chloromethyl ethyl ether, chloromethyl propyl ether, chloromethyl butyl ether, chloromethyl hexyl ether, chloroethyl ethyl ether, chloroethyl butyl ether, chloromethyl vinyl ether, chloroethyl vinyl ether, chloromethyl allyl ether, chloromethyl methallyl ether, chloroethyl vinyl ether, chloroethyl allyl ether, chloroethyl methallyl ether, chloroallyl methyl ether, chloromethallyl ethyl ether, chloromethyl phenyl ether, chloromethyl naphthyl ether, chloromethyl benzyl ether, chloromethyl phenethyl ether, chloroethyl benzyl ether, chlorophenyl methyl ether, chlorobenzyl propyl ether, chloromethylphenyl methyl ether, chloromethyldiphenyl methyl ether, chloromethyl tolyl ether, chloromethyl nitrophenyl ether, chloromethyl cyanophenyl ether, chloromethyl aminophenyl ether, chloromethoxy benzoic acid, chloromethyl sulfophenyl ether, chloromethoxyphenyl methyl ether, methyl chloromethoxybenzoate chloromethylstyryl ether, chloromethoxyphenyl phenyl ether, chloromethoxyphenyl phenyl sulfon, and chloronitrophenyl ethyl ether.

As heterocycle-containing halides, may be mentioned for example chloropyridine, chloroquinolin, chloroacridine, chlorofuran, ethyl chlorothiophen, chlorobenzofuran, chlorodioxane, chlorobenzothiophen, chloroethylpiperidine, chloroethylpyridine, N-chloropentylpiperidine, N-chloromethyl carbazole, N-chloropropyl carbazole, epichlorohydrin, methylepichlorohydrin, chloromethylfuran, chloroethylfuran, chloromethyl nitrofuran, chloroethylthiophen, chloromethylthiophen, bischloromethylthiophen, chlorobutylthiophen, chloromethylbenzophenone, and chloromethylphenyl dihydrobenzofuran.

Examples of heteroatom-containing halides include for example chloropropionitrile, chlorobutylonitrile, chlorovaleronitrile, chloroacrylonitrile, chloronitroethane, chloronitropropane, dichloropropionitrile, dichloronitroethane, dichloronitropropane, chloroethane sulfonic acid, chloropropane sulfonic acid, chlorobutane sulfonic acid, chloroethylamine, chloropropylamine, N-(chloroethyl)dimethyl amine salts, N-(chloroethyl)diethylamine salts, chloromethyl methyl sulfido, chloromethyl ethyl sulfido, and chloroethyl ethyl sulfido.

Among the halogen-substituted compounds exemplified above, those containing no substituent groups, which in turn contain one or more heteroatoms, are preferred in allowing the reaction to proceed efficiently where such compounds contain one or more aromatic rings therein. As halogen-substituted compounds suitable to cause the reaction to take place more efficiently, alkyl halides, alkyl polyhalides, alkylaryl halides, alkenyl halides, carboxylic halides, heterocycle-containing halides, etc. may be used. The reactivity of each of such halogen-substituted compounds varies depending on the conformation of a carbon atom to which a halogen atom is attached. For the reaction of this invention, it is preferable to employ a compound which has one or more halogen atoms substituted at a primary or secondary carbon.

The reaction solvent used in the present invention may be selected from aprotic polar solvents, including, for example, acetonitrile, dioxane, nitromethane, nitroethane, nitrobenzene, pyridine, dimethoxyethane, tetrahydrofuran, tetrahydropyran, 2-meth-1-ytetrahydrofuran, benzonitrile, N,N-dimethylformamide, N,N-dimethylacetamide, N,N-diethylformmide, dimethylsulfoxide, N-methylpyrrolidone, hexamethyl phosphoramide sulforan, orepane and glimes such as monoglime, diglime, triglime and tetraglime. Among the above solvents, acetonitrile, N,N-dimethylformamide, N,N-dimethylacetamide, dimethylsulfoxide, sulforan and tetraglime may be used as particularly preferable solvents. These solvents generally have strong miscibility with water and thus tend to induce mixing of water due to water absorption or upon recycling for re-use. Therefore, care must be exercised upon handling such solvents.

In a reaction system for carrying out the process of this invention, it is necessary that the reaction is initiated while at least a part of the strongly basic substance is suspended therein. In this state, water is present normally in an amount of 6% by weight or so in the reaction system. If the water content exceeds this figure, side reactions such as hydrolysis of a halogen-substituted compound or amide compound tend to occur easily, thereby considerably lowering the yield of an intended product. To make the reaction to proceed efficiently and to increase the yield of an intended product, as will be appreciated from Examples 3 and 4 and Comparative Example 4, it is required to control the water content in the reaction system below at most 5% by weight, preferably, below 2.5% by weight, and more preferably, below 10,000 ppm.

There is no special limitation to the amount of solvent to be employed. However, it may account for 5–95% by weight, preferably, 10–90% by weight of the whole weight of the reactants including the solvent per se.

Next, the strongly basic substance to be employed in the present invention is required to be a solid material and, when dissolved or suspended in water, to make the pH of the aqueous solution be at least 10, preferably, above 11. However, where an ion-exchange resin or other ion-exchange substance is employed, it is exempted from the above requirements. Requirements for such an ion-exchange resin or other ion-exchange substance will be explained later. As such strongly basic substances, there are for example alkali metal oxides, alkaline earth metal oxides, alkali metal hydroxides, alkaline earth metal hydroxides, alkali metal carbonates, alkali methyl hydrides, alkaline earth metal hydrides, alkali metal amides, alkali metal alkoxides, ion-exchange resins and other ion-exchange substances.

Specific examples of the above materials or substances are as follows:

As alkali metal oxides, may be mentioned for example sodium oxide, potassium oxide, lithium oxide, rubidium oxide, and cesium oxide. Exemplary alkaline earth metal oxides include for example beryllium oxide, magnesium oxide, calcium oxide, strontium oxide and barium oxide. Among alkali metal hydroxides, may be mentioned for example sodium hydroxide, potassium hydroxide, lithium hydroxide, rubidium hydroxide, and cesium hydroxide. As alkaline earth metal hydroxides, may be mentioned for example beryllium hydroxide, magnesium hydroxide, calcium hydroxide, strontium hydroxide and barium hydroxide.

Exemplary alkali metal carbonates are for example sodium carbonate, potassium carbonate, lithium carbonate, rubidium carbonate and cesium carbonate. As alkali metal hydrides, may be mentioned for example sodium hydride, potassium hydride, and lithium hydride. As alkaline earth metal hydrides, may be mentioned for example beryllium hydride, magnesium hydride and calcium hydride. Alkali metal amides are alkali metal-substituted compounds of ammonia and include for example sodium amide, potassium amide, and lithium amide. Alkali metal alkoxides are each a compound obtained by substituting the proton of an hydroxyl group of an alcohol and embrace for example sodium methoxide, sodium ethoxide, sodium t-butoxide, potassium methoxide, potassium ethoxide, and potassium t-butoxide.

As an ion-exchange resin, either OH-type or free-type strong basic resin can be employed. The ion-exchange resin contains water preferably in an amount of 15% or less. As other ion-exchange substances, any substances may be used as far as they induce an anion exchange phenomenon. Exemplary ion-exchange substances include anion-exchange cellulose, anion-exchange Sephadex, anion-exchange solutions, basic dolomite, hydrated iron oxide, and hydrated zirconium oxide. They must be in a form capable of undergoing a neutralization reaction with hydrochloric acid.

Among the strongly basic substances described above, as substances suitable for practising the process of this invention, may be mentioned for example alkali metal hydroxides, alkaline earth metal hydroxides, alkali metal oxides, alkaline earth metal oxides, alkali metal carbonates, ion-exchange resins and other ion-exchange substances. As particularly preferred substances, may be mentioned for example alkali metal hydroxides, alkaline earth metal hydroxides, alkali metal oxides, alkaline earth metal oxides, alkali metal carbonates, ion-exchange resins and other ion-exchange substances.

These strongly basic substances are generally subjected to their respective reactions in a solid form and the reactions are initiated while at least parts of the substances still remain in a suspended state.

In practising this invention, the relative amounts of the raw materials, starting amide compound, halogen-substituted compound and strongly basic substance to be used vary depending on the reactivity between the halogensubstituted compound and starting amide compound or depending whether the intended product is an N-monosubstituted amide compound or an N,N-disubstituted amide compound, or by another reason. It is thus rather difficult to limit their relative amounts to specific ranges. However, generally speaking, where an N-monosubstituted amide is intended, the halogen-substituted compound may be used in an amount of 0.2–10 moles, more preferably, 0.3–7 moles per mole of the starting amide compound. On the other hand, the strongly basic substance may be used in an amount of 0.3–10 moles, more preferably, 0.5–7 moles per mole of the starting amide compound.

When producing an N,N-disubstituted amide compound, the halogen-substituted compound may be used in an amount of 1.0–20 moles, more preferably, 1.5–15 moles per mole of the starting amide compound.

It is also possible to produce an N,N-disubstituted amide compound having different substituent groups. Here, two halogen-substituted compounds of different types may be reacted simultaneously with the starting amide compound The relative amounts of the two halogen-substituted compounds of different types vary depending on their reactivity. One of the halogen-substituted compounds may be used generally in an amount of 1.0–20 moles, preferably, 1.0–15 moles per mole of the other halogen-substituted compound, the reactivity of the latter compound being supposed to be high. Also, as a process for producing an N,N-disubstituted amide compound whose substituent groups are different, it may be possible to react the starting amide compound with a first halogen-substituted compound to obtain an N-monosubstituted amide compound and then to react the N-monosubstituted amide compound with a second halogen-substituted compound. When an unsaturated amide compound is employed as a starting amide compound, it is preferable to incorporate a polymerization inhibitor to avoid the polymerization of raw materials and reaction product during the reaction step or purification step. The polymerization inhibitor is not necessarily be limited to any specific one, but, may generally be mentioned phenoltype polymerization inhibitors, amine-type polymerization inhibitors, mercaptan-type polymerization inhibitors, and copper powder.

To carry out the reaction, a conventional reaction tank may be used. However, where a strongly basic substance having low solubility is used, the basic substance may be packed in a column and a mixture solution of a starting amide compound and halogen-substituted compound may be recycled through the column. From the standpoint of the maintenance and control of the reaction facilities, it is more convenient to use a reaction tank.

When carrying out he reaction in a reaction tank, the raw materials may be charged in an arbitrary order. However, where a halogen-substituted compound having high reactivity is employed, it is convenient for the purpose of suppressing side reactions to add the halogen-substituted compound lastly so that it undergoes an intended reaction with the other two raw materials.

The reaction temperature depends on the reactivity of a starting amide compound and halogen-substituted compound to be used. However, a low reaction temperature tends to retard the proceeding of the reaction whereas a high reaction temperature induces side reactions such as hydrolysis of the amide compounds and leads to a low yield. Accordingly, the reaction is usually carried out in a temperature range of $-20°–10020$ C., preferably, $-10°–70°$ C. Except for certain specific halogen-substituted compounds, the reaction temperature is more preferably in the range of $0°–50°$ C. As long as the reaction temperature is kept within the above temperature ranges, it is not always necessary to keep the temperature constant during the reaction. The reaction temperature may be suitably set while maintaining a full control on the progress of the reaction so as to allow the reaction to take place efficiently.

The reaction time varies, similar to the reaction temperature, depending on the types of starting amide compound and halogen-substituted compound to be used. It is however within 30 hours at the longest, generally, within 10 hours. The progress of the reaction may be determined by watching the state of the reaction system or by checking the concentrations of the raw materials and intended product in the reaction system by virtue of gas chromatography or high-speed liquid chromatography.

Upon completion of the reaction, by-produced metal chloride is filtered off in a known manner and, by subjecting the filtrate to a distillation under a reduced pressure, the intended product of high purity is obtained. However, where the metal chloride is dissolved in the reaction solution or sublimable starting amide compound remains in the reaction solution, the solvent is distilled off from the reaction solution and the above substance is then removed with a mixed solvent, which forms two layers, such as benzene-water, chloroform-water or the like. Upon subjecting the organic layer to a distillation under a reduced pressure, the intended product can be obtained with high purity. Where the intended product has a high boiling point or tends to decompose by heat, it may be purified in accordance with a purification method such as solvent extraction or recrystallization.

Moreover, where the reaction solvent has great miscibility with water, such as dimethyl sulfoxide and the intended product is highly hydrophobic such as an N-alkylsubstituted amide compound, it is possible to add water to the reaction solution after the completion of the reaction and separate the intended product as an oil layer, or to extract the intended product with a solvent capable of forming two layers with water, such as benzene, toluene, or chloroform.

According to this invention, it is possible to economically produce N-substituted amide compounds which have an extremely wide variety of functions. Thus, N-substituted amide compounds can be supplied to various application fields, to which conventional N-substituted amide compounds could not be applied.

Since the present invention is carried out with the same reaction pattern, it brings about an advantage that many types of N-substituted amide compounds can be produced in the same reaction vessel, thereby making the process of this invention suitable for the production of many types of N-substituted amide compounds in small quantities.

The invention will further be explained by reference to the following examples:

EXAMPLE 1

Preparation of N-n-Propylacrylamide

To 150 ml of N,N-dimethylformamide, was added and suspended 14 g of potassium hydroxide, followed by a further addition of 14 g of acrylamide and 0.05 g of phenothiazine as polarization inhibitor. The mixture was subjected to a reaction for 3 hours, at 40° C., and with stirring. After the reaction, the reaction solution was analyzed by gas chromatography, using a column packed with 20M of polyethylene glycol. As a result, it was confirmed that N-n-propylacrylamide had been formed in a true weight of 21 g(conversion: 92%). The reaction solution was filtered and N,N-dimethylfofmamide and unreacted n-propylbromide were distilled off under a reduced pressure.

After adding 100 ml of benzene and 50 ml of distilled water to the residue and stirred thoroughly, the solution was separated into two layers. The aqueous solution layer was extracted twice with 50 ml of benzene. The resulting benzene layers were combined together and dried with magnesium sulfate. Then, the benzene layer was subjected to a distillation under reduced pressure. A fraction was collected at 81°–83° C./ 1 mmHg, thereby obtaining 18 g. of N-n-propylacrylamide(yield: 79%).

In the above reaction, the water content in the reaction system was about 1000 ppm or so. Under such a low content of water, the conversion of acrylamide was 95% and the selectivity to N-n-propylacrylamide was 97%.

COMPARATIVE EXAMPLE 1

Preparation of N-N-propylacrylamide

To 150 ml of t-butanol containing 22 g of potassium t-butoxide dissolved therein, was added at room temperature 14 g of acrylamide. The resulting mixture was allowed to stand until the deposition of N-potassiumacrylamide was completed. Then, 31 g of n-propylbromide and 0.05 g of phenothiazine were incorporated and thereafter allowed to react for 3 hours with stirring. Thereafter, deposited potassium bromide was filtered off. The filtrate was subjected to a distillation under a reduced pressure. At 81°-83° C./ 1 mmHg, a fraction was collected, thereby obtaining 6.0 g of N-n-propylacrylamide(yield: 25%).

COMPARATIVE EXAMPLE 2

To 150 ml of N,N-dimethylformamide, were added 14 g of potassium hydroxide, 14 g of, acrylamide and 0.05 g of phenothiazine. The reaction mixture was allowed to initiate a reaction at 40° C.

Thirty minutes after the initiation of the reaction, a white substance deposited on the surfaces of particles of potassium hydroxide and further agitation was not feasible. The reaction mixture was allowed to react for further one hour in the same state and, then, 31 g of n-propyl bromide was added and the reaction was continued for further two hours. The treatment of the reaction mixture was carried out in the same manner as in Example 1. N-n-Propylacrylamide was obtained in an amount as little as 20 g only(yield: 9%).

EXAMPLE 2

Preparation of N-Acetoxyethylacetamide

Ten grams of sodium hydroxide was suspended in 50 ml of N,N-dimethylacetamide, followed by a further addition of 12 g of acetamide, 0.05 g of phenothiazine and 36 g of 2-chloroethyl acetate. A reaction was allowed to take place at 40° C. for 4 hours with stirring. After the completion of the reaction, the reaction solution was filtered to separate off all the undissolved materials. Under reduced pressures, N,N-dimethylacetoamide and unreacted 2-chloroethyl acetate were distilled off. After adding 100 ml of benzene and 50 ml of distilled water to the residue, the mixture was thoroughly agitated and separated into two layers. The aqueous solution layer was extracted twice with 50 ml of benzene. The benzene layers were combined and dried with magnesium sulfate. The thus-dried benzene layer was subjected to a distillation under reduced pressure. A fraction was collected at 138-140° C./ 2 mmHg, thereby obtaining 22 g of N-acetoxyethylacetamide (yield: 74%). The reaction system in the above reaction contained water of the order of 5000 ppm or so.

COMPARATIVE EXAMPLE 3

Preparation of N-acetoxyethylacetamide

To 150 ml of liquid ammonia in which 7.8 g of sodium amide had been dissolved, was added 12 g of acetamide and the reaction mixture was reacted at room temperature for 5 hours in a pressure-resistant reaction tube. Then, 57 g of 2-chloroethyl acetate was added to the reaction solution, followed by a further reaction for 3 hours at room temperature. After the completion of the reaction, ammonia was distilled off and 10% aqueous hydrochloric acid solution was added to the resulting residue so as to obtain an aqueous solution of pH 5. The aqueous solution was extracted twice with 100 ml of ethylacetate. The ethylacetate layers were dried with magnesium sulfate, followed by the distillation-off of ethylacetate. The residual substance was subjected to a distillation under reduced pressure but the intended product, N-acetoxyethylacetamide(138°-140° C./ 2 mmHg) did not come out.

EXAMPLE 3

Preparation of N-n-Propylacrylamide

A reaction and treatment after the reaction were carried out in the same manner as in Example 1, except for the use of N,N-dimethylformamide containing 3.5% by weight of water. The reaction was initiated, similar to Example 1, while potassium hydroxide remained in the suspended state. In this reaction, the conversion, selectivity and yield were 93%, 90% and 84% respectively. The water content in the reaction system was 2.5 % by weight.

EXAMPLE 4

Preparation of N-n-Propylacrylamide

A reaction and treatment after the reaction were carried out in the same manner as in Example 1, except for the use of N,N-dimethylformamide containing 7.0% by weight of water. The reaction was initiated, similar to Example 1, while potassium hydroxide remained in the suspended state. In this reaction, the conversion, selectivity and yield were respectively 87%, 81% and 70%. The reaction system contained water in an amount of 5.0% by weight.

COMPARATIVE EXAMPLE 4

Preparation of N-n-Propylacrylamide

To 150 ml of N,N-dimethylformamide, were added 14 g of acrylamid.e, 0.05 g of phenothiazine and 31 g of n-propyl bromide. After stirring the mixture to dissolve the latter in the former, 19.9 ml of a 47.5% aqueous solution of potassium hydroxide was added to initiate a reaction. At this stage, the reaction solution was separated in two layers and potassium hydroxide was in a completely dissolved state. Thereafter, the procedure of Example 1 was followed exactly. In this reaction, the conversion, selectivity and yield were 63%, 48% and 30% respectively. The reaction system contained water in an amount of 7.2% by weight.

EXAMPLES 5-13

With the combinations of raw materials, strongly basic substances and solvents described in Table 1, their respective reactions were carried out under the reaction conditions also described in Table 1. In Examples 8-13, each reaction was conducted by adding 0.05 g of phenothiazine. After the completion of each reaction, the resulting reaction solution was treated in the same manner as in Example 1, thereby giving results shown in Table 2.

TABLE 1

| Example | Amide compound (g) | Halogen-substituted compound (g) | Strongly basic substance (g) | Solvent (ml) | Reaction temp. (°C.)/ reaction time (hr.) |
|---|---|---|---|---|---|
| 5 | Acetamide (12) | Ethylbromide (21) | Potassium hydroxide (12) | DMF (150) | 30/3 |
| 6 | Acetamide (12) | n-Propylchloride (20) | Sodium hydroxide (9) | DMF (150) | 40/3 |
| 7 | Acetamide (12) | Laurylbromide (75) | Sodium oxide (14) | DMSO (150) | 40/4 |
| 8 | Acrylamide (14) | n-Heptylchloride (33) | Potassium hydroxide (12) | DMF (150) | 40/4 |
| 9 | 2-Ethoxyacrylamide (23) | n-Propylchloride (24) | Potassium hydroxide (12) | Nitromethane (150) | 40/3 |
| 10 | Acrylamide (14) | i-Propylbromide (36) | Potassium hydroxide (16) | DMF (150) | 40/4 |
| 11 | Methacrylamide (17) | Chloromethyl ethyl ether (33) | Potassium hydroxide (16) | DMF (150) | 40/4 |
| 12 | Acrylamide (14) | 2-Bromoethyl acrylate (53) | Potassium hydroxide (16) | DMF (150) | 40/4 |
| 13 | Acetamide (12) | N—(5-bromopentyl) piperidine (70) | Potassium hydroxide (16) | DMF (150) | 40/4 |

Note: DMF: N,N—Dimethylformamide; DMSO: Dimethylsulfoxide

TABLE 2

| Example | Reaction product | Dist'n conditions (temp. °C./press. mmHg) | Yield (g) |
|---|---|---|---|
| 5 | N—Ethylacetamide | 87–89/7 | 12 |
| 6 | N—n-Propylacetamide | 98–100/16 | 16 |
| 7 | N—Laurylacetamide | 224–229/17 | 29 |
| 8 | N—Heptylacrylamide | 118–120/2 | 24 |
| 9 | N—n-Propyl-2-ethoxyacrylamide | 120–121/10 | 24 |
| 10 | N—i-Propylacrylamide | 85–88/1 | 15 |
| 11 | N—Ethoxymethylmethacrylamide | 98–100/0.5 | 20 |
| 12 | N—2-Acrylethylacrylamide | 118–120/0.15 | 24 |
| 13 | N—5-Piperidinopentylacetamide | 170–171/2 | 33 |

EXAMPLE 14

Preparation of N,N-Dimethylacetamide

To 150 ml of acetonitrile, were added 12 g of acetamide and 18 g of sodium hydroxide. While stirring the mixture, 30g of methylchloride was blown into the mixture at 50° C. and a reaction was carried out for 3 hours. After the completion of the reaction, undissolved substances were filtered off and the filtrate was distilled. A fraction was collected at 166°–167° C./760 mmHg, thereby providing 16 g of N,N-dimethylacetamide(yield: 90%).

EXAMPLES 15-26

With the combinations of the raw materials, strongly basic substances and solvents shown in Table 3, their respective reactions were carried out under the reaction conditions also shown in Table 3. In Examples 16, 20, and 23-26, 0.05 g of phenothiazine was added prior to the reactions.

After the completion of reactions, resulting reaction solutions were treated in the same manner as in Example 14. The reaction products given in Table 4 were isolated under their respective distillation conditions shown in the same table.

TABLE 3

| Example | Amide compound (g) | Halogen-substituted compound (g) | Strongly basic substance (g) | Solvent (ml) | Reaction temp. (°C.)/ reaction time (hr.) |
|---|---|---|---|---|---|
| 15 | Lauramide (40) | Methylchloride (29) | Potassium hydroxide (25) | HMPA (150) | 40/3 |
| 16 | Acrylamide (14) | Methylchloride (31) | Potassium hydroxide (25) | DMF (150) | 40/3 |
| 17 | Benzamide (24) | Methylchloride (29) | Sodium hydroxide (18) | DMF (150) | 40/3 |
| 18 | Cyclohexane carboxamide (25) | Methylchloride (30) | Sodium hydroxide (18) | Acetonitrile (150) | 50/3 |
| 19 | Urea (12) | Methylchloride (50) | Potassium carbonate (62) | DMF (150) | 50/3 |
| 20 | 3-Ethoxyacrylamide (23) | Methylchloride (31) | Barium hydroxide (103) | Diglime (200) | 50/3 |
| 21 | Acetamide (12) | Ethylchloride (32) | Barium oxide (92) | Dioxane (200) | 50/3 |
| 22 | P—Nitrobenzamide (33) | Ethylbromide (54) | Lithium hydroxide (15) | Benzonitrile (200) | 50/3 |
| 23 | Acrylamide (14) | 1,4-Dichlorobutane (38) | Potassium hydroxide (22) | DMSO (150) | 40/4 |
| 24 | Ethoxyacetamide (21) | Allylchloride (39) | Sodium hydroxide (20) | THF (150) | 40/3 |
| 25 | Methacrylamide (17) | Methyl chloroacetate (76) | Potassium hydroxide (18) | DMF (150) | 40/5 |

TABLE 3-continued

| Example | Amide compound (g) | Halogen-substituted compound (g) | Strongly basic substance (g) | Solvent (ml) | Reaction temp. (°C.)/ reaction time (hr.) |
|---------|---|---|---|---|---|
| 26 | n-Butylamide (17) | 2-Chloroallyl chloride (66.6) | Potassium hydroxide (18) | DMF (150) | 40/5 |

Note: HMPA: Hexamethylphosphoramide; THF: Tetrahydrofuran

TABLE 4

| Example | Reaction product | Dist'n conditions (temp. °C./press. mmHg) | Yield (g) |
|---------|---|---|---|
| 15 | N,N—Dimethyllauramide | 178–180/15 | 39 |
| 16 | N,N—Dimethylacrylamide | 80–81/20 | 16 |
| 17 | N,N—Dimethylbenzamide | 131–133/15 | 25 |
| 18 | N,N—Dimethylcyclohexane carboxamide | 119–121/12 | 27 |
| 19 | Tetramethylurea | 89–91/18 | 14 |
| 20 | 3-Ethoxy-N,N—dimethylacrylamide | 118–120/6 | 17 |
| 21 | N,N—Diethylacetamide | 93–94/35 | 14 |
| 22 | p-Nitro-N,N—diethylbenzamide | 212–214/18 | 29 |
| 23 | 1-Acryloyl-pyrrolidine | 106–108/10 | 19 |
| 24 | 2-Ethoxy-N,N—diallylacetamide | 74–75/0.6 | 28 |
| 25 | N,N—Bis(methoxycarbonylmethyl) methacrylamide | 144–145/1 | 23 |
| 26 | N,N—Bis(2-chloroallyl)-n-butylamide | 180–182/15 | 33 |

EXAMPLE 27

Preparation of 2-Phenyl-N-n-butylacetamide

To 150 ml of N,N-dimethylformamide, were added 14 g of potassium hydroxide, 27 g of phenylacetamide and 41 g of n-butyl bromide. The mixture was subjected to a reaction at 40° C. for 4 hours. After the completion of the reaction, the reaction solution was analyzed through high-speed liquid chromatography, using a column packed with silica which had been pretreated with octadecyl silane. As a result, it was confirmed that 2-phenyl-N-n-butyl-acetamide had been prepared in a true amount of 34 g (yield: 89%). After subjecting the reaction solution to filtration to remove any substances which had not been dissolved, N,N-dimethylformamide and unreacted n-butyl bromide were distilled off under reduced pressure from the filtrate. The residue was mixed with 100 ml of benzene and 50 ml of distilled water. They were thoroughly stirred and then separated into two layers. The aqueous solution layer was then extracted twice with 50 ml of benzene. All the benzene layers were combined and dried with magnesium sulfate. The residue, resulted from a distillation under reduced pressure of the benzene layers, was recrystallized from benzine, thereby obtaining 30 g of 2-phenyl-N-n-butyl-acetamide having a melting point of 56°–57° C.(yield: 78%).

EXAMPLES 28–50

With the combinations of raw materials, strongly basic substances and solvents given in Table 5, their respective reactions were carried out under reaction conditions shown in the same table. In Examples 29–33, 44 and 45, 0.05 g of phenothiazine was added prior to the reactions.

After the completion of the reactions, the resulting reaction solutions were treated in the same manner as in Example 27. The reaction products shown in Table 6 were obtained in a crystalline form from the recrystallization solvents given in the same table.

TABLE 5

| Example | Amide compound (g) | Halogen-substituted compound (g) | Strongly basic substance (g) | Solvent (ml) | Reaction temp. (°C.)/ reaction time (hr.) |
|---------|---|---|---|---|---|
| 28 | Benzamide (24) | Cyclohexyl methyl chloride (40) | Sodium hydroxide (11) | DMF (150) | 40/4 |
| 29 | Methacrylamide (17) | Cyclohexylbromide (49) | potassium hydroxide (15) | DMF (150) | 50/4 |
| 30 | Methacrylamide (17) | 4-Bromotoluene (51) | Potassium hydroxide (15) | DMF (150) | 60/3 |
| 31 | Benzamide (24) | 4-Chloromethyl-m-xylene (39) | Potassium hydroxide (15) | $DMA_c$ (150) | 50/3 |
| 32 | Methylacrylamide (17) | p-Bromoanisole (46) | Potassium hydroxide (15) | DMF (150) | 70/3 |
| 33 | Acrylamide (14) | 4-Bromostyrene (38) | Potassium hydroxide (15) | DMF (150) | 70/3 |
| 34 | Benzamide (24) | 2-Chloroethyl-benzene (35) | Sodium hydroxide (11) | Dimethoxy ethane (150) | 40/4 |
| 35 | Benzamide (24) | Cyclohexylchloride (47) | Potassium hydroxide (16) | DMF (150) | 60/3 |
| 36 | Cyclohexane carboxamide (25) | 2-Chloroethyl benzene (35) | Sodium hydroxide (10) | DMF (150) | 40/4 |
| 37 | 3-Cyclohexyl propioamide (31) | Cyclohexylbromide (41) | Potassium hydroxide (16) | DMF (150) | 60/3 |
| 38 | Acetamide (12) | Diethyl 2-bromo- | Potassium | DMF | 50/3 |

TABLE 5-continued

| Example | Amide compound (g) | Halogen-substituted compound (g) | Strongly basic substance (g) | Solvent (ml) | Reaction temp. (°C.)/ reaction time (hr.) |
|---|---|---|---|---|---|
| | | malonate (59) | hydroxide (15) | (150) | |
| 39 | p-Nitrobenzamide (33) | 2-Chloroethyl p-nitrobenzoate (51) | Potassium hydroxide (15) | DMF (150) | 50/3 |
| 40 | Acetamide (12) | 1-Chloromethyl naphthalene (32) | Sodium hydroxide (10) | Nitroethane (150) | 40/4 |
| 41 | Acetamide (12) | 1-Bromonaphthalene (39) | Potassium hydroxide (16) | DMF (150) | 50/3 |
| 42 | Acetamide (12) | 3-Bromoacridine (49) | Potassium hydroxide (15) | DMF (150) | 60/3 |
| 43 | Acetamide (12) | 3-Chloropropionitrile (22) | Potassium hydroxide (15) | Benzonitrile (150) | 50/3 |
| 44 | Cinnamide (29) | Bromobenzene (39) | Potassium hydroxide (15) | Nitromethane (150) | 60/3 |
| 45 | Malonamide (20) | Benzylchloride (42) | Potassium hydroxide (29) | DMF (150) | 40/4 |
| 46 | Adipamide (29) | Benzylchloride (41) | Sodium hydroxide (20) | DMF (150) | 40/4 |
| 47 | Furmaramide (23) | Benzylchloride (41) | Potassium hydroxide (29) | DMF (150) | 40/4 |
| 48 | Terephthalamide (33) | Benzylchloride (41) | Potassium hydroxide (29) | DMF (150) | 40/4 |
| 49 | Oxamide (17) | Ethyl chloroacetate (64) | Potassium hydroxide (28) | DMF (150) | 50/4 |
| 50 | Urea (12) | Benzylchloride (62) | Sodium hydroxide (20) | DMF (150) | 40/4 |

Note: $DMA_c$ : N,N—Dimethylacetamide

TABLE 6

| Example | Reaction product | M.P. (°C.) | (recry'n solvent) | Yield (g) |
|---|---|---|---|---|
| 28 | N—Cyclohexylmethyl benzamide | 106.0–106.5 | (Ethanol) | 33 |
| 29 | N—Cyclohexyl methacrylamide | 110–111 | (Petroleum ether) | 17 |
| 30 | N—p-Tolylmethacrylamide | 86–87 | (Water-ethanol) | |
| 31 | N—2,4-Dimethylbenzyl-benzamide | 97–98 | (Ethylacetate-petroleum ether) | 35 |
| 32 | N—p-Methoxyphenyl-methacrylamide | 89–90 | (Water-ethanol) | 18 |
| 33 | N—p-Styryl acrylamide | 128–130 | (Water-ethanol) | 17 |
| 34 | N—Phenethyl benzamide | 117–118 | (Water-ethanol) | 34 |
| 35 | N—Cyclohexyl benzamide | 147–148 | (Ethanol) | 20 |
| 36 | N—Phenethyl cyclohexane carboxamide | 93–94 | (Cyclohexane) | 35 |
| 37 | 3,N—Dicyclohexylpropioamide | 108–109 | (Methanol) | 23 |
| 38 | N—(Diethoxycarbonyl)methyl acetamide | 95–97 | (Water) | 41 |
| 39 | N—Nitro-N[2-(4-nitrobenzoyloxy)ethyl]benzamide | 189.5–190.5 | (Acetone) | 48 |
| 40 | N—(1-Napthylmethyl)acetamide | 127–128 | (Ethanol) | 29 |
| 41 | N—1-Napthyl acetamide | 158.5–159.5 | (Ethanol) | 20 |
| 42 | 3-Acetylaminoacridine | 235–236 | (Water-ethanol) | 23 |
| 43 | N—(2-Cyanoethyl)acetamide | 64–65 | (Chloroform-carbon tetrachloride) | 16 |
| 44 | N—Phenyl cinnamide | 138–140 | (Water-ethanol) | 23 |
| 45 | N,N'Dibenzyl malonamide | 140–141 | (Ethanol-benzine) | 42 |
| 46 | N,N'—Dibenzyl adipamide | 188–189 | (Water-ethanol) | 47 |
| 47 | N,N'—Dibenzyl fumaramide | 313–314 | (Ethanol) | 42 |
| 48 | N,N'—Dibenzyl phthalamide | 264–266 | (Acetone) | 49 |
| 49 | N,N'—Bisethoxycarbonyl methyloxamide | 133–134 | (Ethanol) | 34 |
| 50 | N,N'—Dibenzylurea | 170–171 | (Chloroform) | 34 |

EXAMPLE 51

Preparation of N,N,N',N'-Tetramethylfumaramide

To 150 ml of N,N-dimethylformamide, were added 56 g of potassium hydroxide and 23 g of fumaramide. While stirring the mixture, 56 g of methylchloride was blown at 40° C. into the mixture. A reaction was carried out for 4 hours. After the reaction, undissolved substances were filtered off and the resulting filtrate was subjected to distillation under reduced pressure so as to remove the solvent and unreacted raw materials. The residue of the distillation was then recrystallized from ethanol, thereby giving 27 g of N,N,N',N'-tetramethylfumaramide having a melting point of 130°–131° C.(yield: 79%).

EXAMPLES 52-55

With the combinations of the raw materials, strongly basic substances and solvents given in Table 7, their respective reactions were carried out under the reaction conditions also given in the same table. After the completion of each reaction, the reaction solution was treated in the same manner as in Example 51. The reaction products shown in Table 8 were obtained by recrystallizing them from their respective recrystallization solvents also indicated in the same table.

TABLE 7

| Example | Amide compound (g) | Halogen-substituted compound (g) | Strongly basis substance (g) | Solvent (ml) | Reaction temp. (°C.)/ reaction time (hr.) |
|---|---|---|---|---|---|
| 52 | Succinamide (23) | Methylchloride (50) | Potassium hydroxide (50) | DMAC (200) | 40/4 |
| 53 | Phthalamide (16) | Ethylbromide (55) | Sodium hydroxide (37) | DMF (150) | 40/4 |
| 54 | 4,4-Dimethyl-pent-2-inamide (25) | Methylchloride (25) | Sodium hydroxide (18) | DMF (150) | 40/4 |
| 55 | Succinamide (12) | 3-Bromopropionitrile (67) | Potassium hydroxide (28) | DMAC (150) | 40/4 |

TABLE 8

| Example | Reaction product | M.P. (°C.) | (recry'n solvent) | Yield (g) |
|---|---|---|---|---|
| 52 | N,N,N',N'—Tetramethylsuccinamide | 83–86 | (Diethyl ether) | 27 |
| 53 | N,N,N',N'—Tetraethylphthalamide | 38–39 | (Ethyl acetate) | 34 |
| 54 | 4,4,N,N—Tetramethyl pent-2-inamide | 65–66 | (Diethyl ether-petroleum ether) | 23 |
| 55 | Tetrakis-N—2-cyanoethyl succinamide | 175–176 | (Water) | 26 |

EXAMPLE 56

Preparation of N-Allyl-N-ethylacetamide

To 150 ml of N,N-dimethylformamide, were added 30 g of potassium hydroxide, 12 g of acetamide, 54 g of ethyl bromide, 23 g of allyl chloride and 0.05 g of phenothiazine. They were subjected to a reaction under stirring conditions at 30° C. for 5 hours.

After removing undissolved substances from the reaction solution, the filtrate was distilled under reduced pressure. A fraction was collected at 185°–186° C./633 mmHg, thereby providing 18 g of N-allyl-N-ethylacetamide(yield: 70%).

EXAMPLE 57

Preparation of N-2-cyanoethyl-N-methylmethacrylamide

To 150 ml of N,N-dimethylformamide, were added 28 g of potassium hydroxide, 17 g of methacrylamide, 23 g of 3-chloropropionitrile and 0.05 g of phenothiazine. A reaction was carried out at 40° C. for 3 hours with stirring.

After the completion of the reaction, a 20 g portion of the reaction solution was collected. Subsequent to the removal of undissolved substances, the filtrate was distilled under reduced pressure. The distillation residue was recrystallized from water, thereby obtaining 1.8 g of N-2-cyanoethylmethacrylamide having a melting point of 46°–48° C.(yield: 68%). Twenty grams of methyl were blown at 40° C. into the remaining reaction solution under stirring conditions, thereby allowing a reaction to take place for 4 hours. Upon completion of the reaction, undissolved substances were filtered off and the filtrate was distilled under reduced pressure. A fraction was collected at 113°–116° C./1 mmHg, resulting in the preparation of 18 g of N-2-cyanoethyl-N-methylmethacrylamide(yield: 65%).

EXAMPLE 58

Preparation of Diacetylamide

To 150 ml of dioxane, were added 14 g of calcium oxide and 12 g of acetamide. Under stirring conditions, 16 g of acetylchloride was added dropwise at 5° C. A reaction was continued for 2 hours.

After the reaction, undissolved substances were filtered off and the solvent and unreacted raw materials were distilled off from the filtrate. The distillation residue was recrystallized from petroleum ether, obtaining 15 g of diacetylamide having a melting point of 80°–81° C. (yield: 72%).

EXAMPLES 59–63

With the combinations of raw materials, strongly basic substances and solvents given in Table 9, their respective reactions were conducted under the reaction conditions also shown in the same table. In Examples 59 and 60, 0.05 g of phenothiazine was added prior to the reactions.

After each reaction, the reaction solution was treated in the same manner as in Example 58. The reaction products given in Table 10 were recrystallized from their respective recrystallization solvents also shown in the same table.

TABLE 9

| Example | Amide compound (g) | Halogen-substituted compound (g) | Strongly basic substance (g) | Solvent (ml) | Reaction temp. (°C.)/ reaction time (hr.) |
|---|---|---|---|---|---|
| 59 | Acrylamide (14) | Acryloylchloride (18) | Sodium hydroxide (8) | DMF (150) | 5/3 |
| 60 | Methacylamide (17) | Benzene sulfonylchloride (35) | Barium hydroxide (19) | THF (150) | 5/3 |
| 61 | Benzamide (24) | Benzene sulfonylchloride (35) | Calcium hydroxide (9) | DMA$_c$ (150) | 20/3 |
| 62 | Benzamide (24) | Acetylchloride (16) | Sodium hydroxide (8) | Acetonitrile (150) | 5/3 |
| 63 | Malonamide (20) | Acetylchloride (16) | Potassium hydroxide(23) | Dimethoxyethane | 5/3 |

TABLE 9-continued

| Example | Amide compound (g) | Halogen-substituted compound (g) | Strongly basic substance (g) | Solvent (ml) | Reaction temp. (°C.)/ reaction time (hr.) |
|---|---|---|---|---|---|
| | | | | (150) | |

TABLE 10

| Example | Reaction product | M.P. (°C.) | (recry'n solvent) | yield (g) |
|---|---|---|---|---|
| 59 | Diacrylamide | 176–178 | (methanol-benzene) | 18 |
| 60 | N—phenylsulfonyl methacrylamide | 128–129 | (water) | 24 |
| 61 | N—phenylsulfonyl benzamide | 146–147 | (ethanol) | 27 |
| 62 | N—acetylbenzamide | 116–117 | (diethylether) | 23 |
| 63 | N,N'—diacetylmalonamide | 137–138 | (ethanol) | 22 |

EXAMPLE 64

Preparation of N-3-Acryloylaminopropyl carbazole

To 150 ml of N,N-dimethylformamide, were added 14 g of acrylamide, 14 g of potassium hydroxide, and 58 g of N-3-bromopropyl carbazole. A reaction was carried out with stirring for 3 hours at 50° C. After the reaction, undissolved substances were filtered off and solvent was removed through distillation from the filtrate. Then, the distillation residue was recrystallized from a mixed solvent of acetone-n-hexane, thereby providing 39 g of N-3-acryloylaminopropyl carbazole having a melting point of 121.5°–122.5° C.(yield: 70%).

EXAMPLE 65

Preparation of N-3-carboxy-2-propenylacetamide

To 150 ml of N,N-dimethylformamide, were added 12 g of acetamide, 14 g of potassium hydroxide, 37 g of sodium 4-chloro-2-butynoate, and 0.05 g of phenothiazine. They were reacted at 50° C. for 4 hours with stirring.

After the reaction, undissolved substances were filtered off and 30 g of conc. hydrochloric acid was added to the filtrate. The solvent and unreacted raw materials were distilled off under reduced pressure. The resulting distillation residue was recrystallized from a mixed solvent of methanol-chloroform, thereby obtaining 16 g of N-3-carboxy-2-propenylacetamide having a melting point of 139°– 140° C.(yield: 56%).

EXAMPLE 66

Preparation of Hippuric Acid

To 150 ml of N,N-dimethylformamide, were added 24 g of benzamide, 14 g of potassium hydroxide and 40 g of sodium bromoacetate. They were reacted at 60° C. for 4 hours with stirring. After the reaction, the reaction solution was treated in the same manner as in Example 65. The resulting distillation residue was recrystallized from distilled water, thereby obtaining 34 g of hippuric acid having a melting point of 187° C.(yield: 69%).

EXAMPLE 67

Preparation of N,N-Bis-6-carboxyhexylacetamide

To 250 ml of N,N-dimethylformamide, were added 12 g of acetamide, 30 g of potassium hydroxide and 116 g of sodium 7-bromoheptanoate. They were reacted at 80° C. for 5 hours with stirring. After the reaction, the reaction solution was treated in the same manner as in Example 65. The resulting distillation residue was recrystallized from a mixed solvent of acetone-diethylether, thereby giving 29 g of N,N-bis-6-carboxylhexylacetamide having a melting point of 73°–74° C.(yield: 45%).

EXAMPLE 68

Preparation of N-Allylcrotonamide

To 200 ml of N,N-dimethylformamide, were added 17 g of crotonamide, 105 g of LEWATIT MP-500(trade mark, product of Beyer AG) which had been subjected to a pretreatment described below, 19 g of allylchloride and 0.05 g of phenothiazine. They were reacted at 40° C. for 5 hours with stirring.

After the reaction, the ion-exchange resin was filtered off and the filtrate was then distilled under reduced pressure. A fraction was collected at 90°–91° C./0.8 mmHg, thereby obtaining 18 g of N-allylcrotonamide (yield: 71%). Treatment of Ion-exchange Resin:

As a strongly basic ion-exchange resin, was used LEVATIT MP-500. The resin was preconditioned and then converted to an OH-type resin with 1N-aqueous sodium hydroxide solution. It was then thoroughly washed with water. After removing water, it was dried at 65° C. for 5 hours.

EXAMPLE 69

Preparation of N-Cyclohexylacetamide

To 200 ml of nitroethane, were added 12 g of acetamide, 105 of MP-500, which was also used in Example 68, and 41 g of cyclohexylbromide. They were reacted at 60° C. for 5 hours with stirring. After the reaction, the ionexchange resin was filtered off and the resulting filtrate was distilled under reduced pressure to remove the solvent and unreacted raw materials. The resulting distillation residue was recrystallized from petroleum ether, thereby obtaining 16 g of N-cyclohexylacetamide having a melting point of 108°–109° C.(yield: 57%).

EXAMPLE 70

Preparation of N-Benzylacetamide

To 200 ml of N,N-dimethylformamide, were added 12 g of acetamide, 105 g of LEVATIT MP-500, which was also used in Example 68, and 32 g of benzylchloride. They were .reacted at 50° C. for 4 hours with stirring. After the reaction, the reaction solution was treated in the same manner as in Example 69, the resulting distillation residue was recrystallized from benzene, thereby providing 22 g of N-benzylacetamide having a melting point of 61°–62° C.

EXAMPLE 71

Preparation of N-Benzylcrotonamide

To 200 ml of N,N-dimethylformamide, were added 17 g of crotonamide, 105 g of LEVATIT MP-500, which was also used in Example 68, and 32 g of benzylchloride. They were reacted at 50° C. for 4 hours with stirring. After the reaction, the reaction solution was treated in the same manner as in Example 69, the resulting distillation residue was recrystallized from benzine, and 25 of N-benzylcrotonamide having a melting point of 112.5°–113.6° C. was obtained (yield: 71%).

EXAMPLE 72

Preparation of N,N-Dimethylmethacrylamide

To 150 ml of dimethylsulfoxide, were added 17 g of methacrylamide. 0.05 g of phenothiazine and 18 g of sodium hydroxide. While stirring the mixture, 30 g of methylchloride was blown at 40° C. into the mixture. They were reacted for 3 hours. After the reaction, undissolved substances were filtered off. Then, 150 ml of benzene and 150 ml of water were added to the resulting filtrate. They were thoroughly agitated and allowed to stand, resulting in the formation of two separate layers. The benzene layer was placed aside. The water layer was extracted twice with 100 ml of benzene. All the benzene layers were combined and dried with magnesium sulfate. It was thereafter subjected to distillation under reduced pressure. A fraction was collected at 65°–67° C./100 mmHg, thereby obtaining 19 g of N,N-dimethylmethacrylamide(yield: 86%).

EXAMPLE 73

Preparation of N,N-dimethylacrylamide

To 2 ml of dimethylsufoxide were added in suspension 0.17 grams of KOH (base/hydrogen ratio =1.5). After stirring at room temperature for 5 minutes, 0.07 grams of acrylamide and 0.57 grams of methyl iodide were added for effecting reaction with agitation for 5 minutes. After the reaction was completed, the reaction mixture was analyzed by means of gas chromatography using a column with 20M polyethylene glycol. As a result, it was found that 0.090 grams of N,N-dimethylacrylamide were formed (yield 91%).

COMPARATIVE EXAMPLE 5

Preparation of N,N-dimethylacrylamide

The reaction was carried out in the same manner as in Example 73, except that 0.45 grams of KOH (base/hydrogen ratio=8) were used. After the reaction, the mixture was analyzed in the same manner as in Example 73, and it was found that 0.034 grams of N,N-dimethylacrylamide were formed (yield 34%). The degree of conversion of the acrylamide was measured at 99%.

EXAMPLE 74

Preparation of N,N-dimethylmethacrylamide

The reaction was carried out in the same manner as in Example 73, except that 0.085 grams of methacrylamide, instead of the 0.07 grams of acrylamide, were used, and that 0.15 grams of KOH (base/hydrogen ratio=1.4) were also employed. After the reaction, the mixture was analyzed as in Example 73 and it was found that 0.106 grams of N,N-dimethylmethacrylamide were formed (yield 94%).

COMPARATIVE EXAMPLE 6

Preparation of N,N-dimethylmethacrlamide

The reaction was effected in the same manner as in Example 73, except that 0.45 grams of KOH (base/hydrogen ratio=8) were employed. After the reaction, the mixture was analyzed and it was found that 0.043 grams of N,N-dimethylmethacrylamide were formed (yield 38%). The degree of conversion of the methacrylamide was measured at 97%.

It will be noted that in fact in above Example 1, 31g of n-propylbromide were added together with the 14g of acrylamide and 0.05g of phenothiazine to the potassium hydroxide suspension, and further that in the experiment such strongly basic substance was used in an amount of 0.6 moles per mole of replaceable hydrogen of the starting amide compound.

In above Comparative Example 2, the amount of N-n-propylacrylamide obtained was in fact only 2.0g (yield 9%).

In above Example 47, after the completion of the reaction and prior to filtration to remove substances which had not been dissolved, the reaction solution was analyzed through high speed liquid chromatography, using a column packed with silica which had been pretreated with octadecyl silane, and as a result it was confirmed that N,N-dibenzylfumaramide had been prepared in a true amount of 45 g (yield 94%).

Exemplary base/replaceable hydrogen mole ratios (moles of the strongly basic substance per one mole of replaceable hydrogen of the starting amide compound) and corresponding intended product yields of preferred production process examples of this invention from among the above Examples are as follows:

| Example | Base/Hydrogen Mole Ratio | Yield g (%) |
|---|---|---|
| 1 | 0.6 | 18 (79) |
| 3 | 0.6 | — (84) |
| 4 | 0.6 | — (70) |
| 8 | 0.5 | 24 (72) |
| 9 | 0.5 | 24 (76) |
| 10 | 0.7 | 15 (67) |
| 16 | 1.15 | 16 (82) |
| 20 | 1.5 | 17 (60) |
| 23 | 1.0 | 19 (77) |
| 47 | 0.6 | 42 (88) |
| 51 | 1.2 | 27 (79) |
| 72 | 1.1 | 19 (86) |
| 73 | 1.5 | 0.090 (91) |
| 74 | 1.4 | 0.106 (94) |

Examplary results confirming the adverse influence of water in the reaction system on the conversion, selectivity and yield of the intended product of preferred production process examples of this invention from among the above Examples are as follows:

| | Water Content in Reaction System | Conversion % | Selectivity % | Yield % |
|---|---|---|---|---|
| Example | | | | |
| 1 | 1000 ppm | 95 | 97 | 92 |
| 3 | 2.5 wt. % | 93 | 90 | 84 |
| 4 | 5.0 wt. % | 87 | 81 | 70 |
| Comp. Ex. 4 | 7.2 wt. % | 63 | 48 | 30 |

It will be seen from the above Examples and from what is stated hereinafter that, notwithstanding the earlier stated features of the general production process, the present invention is particularly directed to an improved preferred production process for unsaturated N-substituted amide compounds.

It will be realized that unlike aromatic N-substituted amide compounds and saturated N-substituted amide compounds which have a very low polymerization property or no such property, unsaturated amide compounds, i.e. unsaturated aliphatic N-substituted carboxylic acid amide compounds, as earlier stated, have an excellent homopolymerization or copolymerization property. Despite the earlier stated advantages and otherwise wide variety of application fields and usefulness known for such unsaturated N-substituted amide compounds, these compounds have not yet been used in a great quantity as no inexpensive industrial production process has yet been established for them.

In this regard as to the earlier stated known industrial production processes of N-substituted amide compounds, relying upon the reaction between a carboxylic chloride and an amine, as well as another such production process which makes use of the Ritter reaction, under current circumstances such unsaturated N-substituted amide compounds produced in accordance with these stated conventional processes are either expensive or are limited to certain specific types, thereby limiting their applications to specific fields.

As to the earlier stated known two step production process for N-substituted amide compounds, (Hikkinbottom, W. J., *Reactions of Organic Compounds,* Vol. 3, 1957; and U.S. Pat. No. 3,084,191), in which first the amide compound is converted to an amide compound substituted by one or more alkali metals under the influence of a strongly basic substance such as alkali metal alkoxide, and second the thus-alkali metal substituted amide compound is converted to an N-substituted amide compound under the influence of a halogensubstituted compound such as alkyl halide, this process involves the inconvenience, in addition to the need for two separate successive steps, that it requires a protonic solvent such as liquid ammonia or an alcohol as reaction solvent, having high reactivity in the presence of a basic catalyst with a halogen-substituted compound; and an extremely strong basic substance which is irksome to handle, such as an alkali metal amide, alkali metal hydride, or alkali metal alkoxide. As is shown in particular in Comparative Examples 1 and 3 above, this known process involves such problems that the yield of an intended unsaturated N-substituted amide compound final product is low, the halogen-substituted compounds reactable with the alkali metal substituted amide compound are limited to specific ones and the reaction product is exclusively an N-monosubstituted amide compound and, where an N,N-disubstituted amide compound is intended, the process has to be repeated similarly. For the reasons mentioned above, this process has not been adopted in an industrial large scale as a production process for general unsaturated N-substituted amide compounds.

As to the earlier stated alternative known two step production process (G. L. Isele et al., Synthesis, 1971 (5)), in which, after reacting an amide compound with a strongly basic substance in an aprotic polar solvent to form an alkali metal-substituted amide compound, the alkali metal-substituted amide compound is reacted with a halogen-substituted compound such as an alkyl halide to obtain an N-alkyl-substituted-amide compound, even if this process is followed, no satisfactory result is obtained, as is clear from Comparative Example 2 above.

In addition, as to the earlier stated production process of N-alkylated organic compounds (USSR Certificate of Inventorship No. 667,547), in which a basic substance such as caustic soda is added in the form of an aqueous solution and the substitution reaction is initiated while keeping all the basic substance in a liquid state, the presence of water in the reaction mixture is considered extremely convenient for the proceeding of the reaction. As is apparent from a comparison between the above Examples 1, 3 and 4 and Comparative Example 4, this known process is accompanied by a considerable occurrence of reaction by-products, thereby making its selectivity of an intended N-substituted amide compound poor and, depending on an unsaturated N-substituted amide compound intended, resulting in a considerable reduction of its yield.

Lastly, as earlier stated, in the case where the starting amide compound to which the present invention is directed is particularly an unsaturated compound, i.e. unsaturated aliphatic N-substituted amide compound, N,N-substitution reaction does not take place in the same manner as in the case of the saturated compounds disclosed in Johnstone et al. (Tetrahedron, Vol. 35, pages 2169–2173), as is confirmed especially by a comparison between the above Examples 73 and 74 and Comparative Examples 5 and 6. Following the general alkylation procedure recited on page 2173, left column, of the Johnstone et al. reference, which shows an Example of the use of potassium hydroxide in an amount of 4 m moles per replaceable hydrogen of the substrate, i.e. 8 moles per one mole of the substrate, the above Comparison Examples 5 and 6 confirm that in the case where such a large amount of potassium is used in an N-substitution reaction of unsaturated amide compounds, polymerization and other side reactions take place. This may be attributed to the earlier stated excellent homopolymerization or copolymerization property of unsaturated amide compounds in particular.

On the other hand, the above Examples 73 and 74 show that under the particular conditions of the preferred production process of the present invention, the unsaturated N-substituted amide compounds result in high yields of the intended final product. This is further confirmed by the above Examples 1, 3, 4, 8, 9, 10, 16, 20, 23, 47, 51 and 72.

Thus, in accordance with the particular aspects of the preferred production process of the present invention, it is among its special objects to provide a production process, which can produce not only an unsaturated N-monosubstituted amide compound but also an unsaturated N,N-disubstituted amide compound in a single-step reaction; which is substantially free of side reactions and can thus produce an intended unsaturated N-substituted amide compound with good selectivity; and which is suitable for the production of a wide variety of unsaturated N-substituted amide compounds.

According to the particular aspects of this invention, a wide variety of unsaturated N-monosubstituted amide compounds and unsaturated N,N-disubstituted amide compounds can each be produced with a high yield without substantially causing side reactions to occur by an improved preferred production process which comprises bringing a strongly basic substance, a starting amide compound and a halogen-substituted compound into simultaneous contact in an aprotic polar solvent to react them together, including the improvement wherein in the reaction system the starting amide compound is an unsaturated aliphatic monocarboxylic acid amide represented by the general formula $C_nH_{2n-1}CONH_2$ in which n stands for an integer of 2–3, said unsaturated aliphatic amide optionally containing alkoxy substituent groups, or an unsaturated aliphatic dicarboxylic acid amide represented by the general formula $C_nH_{2n-2}(CONH_2)_2$ in which n stands for an integer of 2-3; the strongly basic substance, is an alkali metal hydroxide or an alkaline earth metal hydroxide; the halogensubstituted compound is an alkyl halide, alkyl polyhalide, aralkyl halide or alkenyl halide compound; the amount of the strongly basic substance is 0.5-1.5 moles per mole of replaceable hydrogen of the starting amide compound; the amount of aprotic polar solvent is 10-90% by weight; the amount of water present at the beginning of the reaction is 5% by weight or less; and the reaction is initiated while maintaining the basic substance in a suspended state.

It is clear from the foregoing that the preferred production process according to the particular aspects of this invention features very little occurrence of side reactions and thus a high yield of an intended product. It is capable of producing a wide variety of unsaturated N-substituted amide compounds as it permits reactions between an extremely wide range of amide compounds and an extremely broad variety of halogen-substituted compounds by combining them suitably. Moreover, it enables the production of each of unsaturated N-monosubstituted amide compounds and unsaturated N,N-disubstituted amide compounds in a single-step reaction by selecting suitable production conditions. The above successful preferred production process of the present invention is based on the present inventors' finding that the presence of water in the reaction system, which has heretofore been considered to be convenient, serves to induce side reactions contrary to what has been believed and impedes the production of an intended unsaturated N-substituted amide compound; and, instead of reacting an unsaturated amide compound and a strongly basic substance first and then causing a halogen-substituted compound to react with a reaction product cf the unsaturated amide product and basic substance as proposed by the prior art, it is necessary to bring the strongly basic substance, unsaturated amide compound and halogen-substituted compound into a simultaneous contact to react them together.

Accordingly, either one of the following processes may be suitably selected in the present invention, as earlier stated:

(a) The three starting materials are simultaneously added to and mixed in an aprotic polar solvent and the strongly basic substance is suspended therein to react them together;

(b) The strongly basic substance is suspended in an aprotic polar solvent and the unsaturated amide compound and halogensubstituted compound are then simultaneously supplied into the suspension to react them together; and (c) The unsaturated amide compound and halogen-substituted compound are dissolved or suspended in an aprotic polar solvent and the strongly basic substance is then added and suspended.

According to the particular aspects of the preferred production process of the present invention, the following features are especially contemplated.

Unsaturated aliphatic carboxylic acid amides are represented by the general formula $C_nH_{2n-1}CONH_2$, in which n stands for an integer of 2-3. These amides contain at least one carbon-to-carbon double bond in their molecules. Also included are those containing alkoxy substituent groups.

Exemplary unsaturated aliphatic monocarboxylic acid amides include acrylamide, methacrylamide, vinylacetamide, crotonamide, ethoxyacrylamide and ethoxymethacrylamide.

Unsaturated aliphatic dicarboxylic acid amides are represented by the general formula $C_nH_{2n-2}(CONH_2)_2$ in which n stands for an integer of 2-3.

Exemplary unsaturated aliphatic dicarboxylic acid amides include maleamide and fumaramide and citraconamide.

As a halogen-substituted compound to be reacted with a starting amide compound, a wide variety of compounds may be mentioned, including for example alkyl halides, alkyl dihalides, aralkyl halides and alkenyl halides.

Alkyl halides are represented by the general formula $C_nH_{2n+1}X$, in which X denotes a halogen atom and n is an integer of 1-20. Alkyl polyhalides are represented by the general formula $C_nH_{2n+2-m}X_m$, in which X means a halogen atom and n and m are respectively integers of 1-20 and 2-4.

Alkenyl halides are unsaturated halogen-substituted compounds represented by the general formula $C_nH_{2n+2-m-2r}X_m$, in which X means a halogen atom and n, m and r are all integers and stand respectively for 2-10, 1-4 and 1-4.

Aralkyl halides are represented by the general formula $Ar_m \cdot C_nH_{2n+2-m-r}X_r$, in which X and Ar denote respectively a halogen atom and an aromatic ring and n, m and r are all integers and stand respectively for 1-20, 1-4 and 1-4. Here, as the aromatic ring, a benzene, naphthalene or anthracene ring may be employed. Also included are those containing at least one of at least one type of substituent groups such as alkyl, alkenyl and aryl groups and halogen atoms, such substituent groups and/or atoms being attached to the aromatic ring.

Although each of chlorine-substituted, bromine-substituted and iodine-substituted compounds are encompassed by the preferred production process of the present invention, the following chlorine-substituted compounds are given as representative examples of halogen-substituted compounds. Where two or more halogen atoms are incorporated, it is not necessary that such substituent halogen atoms be the same. They may be combinations of chlorine(s)-bromine(s) chlorine(s)-iodine(s) and bromine(s)-iodine(s) However, in the following specific examples of halogen-substituted compounds, substituent halogen atoms are limited to substituent chlorine atoms only.

As alkyl halides, may be mentioned for example chloromethane, chloroethane, chloropropane, chlorobutane, chloropentane, chlorohexane, chloroheptane, chlorodecane, chlorododecane, chlorotetradecane, and chlorooctadecane. Among alkyl polyhalides, there are for example dichloromethane, chloroform, tetrachloromethane, dichloroethane, trichloroethane, tetrachloroethane, dichloropropane, trichloropropane, dichlorobutane, dichloroheptane, dichlorohexane, and dichlorodecane.

Among aryl alkyl halides, i.e. aralkylhalides, may be mentioned for example benzychloride, benzylidenedichloride, phenethylchloride, phenylpropylchloride, chloromethylnaphthalene, chloromethylanthracene, diphenylmethylchloride, triphenylmethylchloride, chloromethyltoluene, chloromethylethylbenzene, chloromethylxylene, chloromethylstyrene, chloromethylbiphenyl and chlorobenzylchloride.

As alkenyl halides, may be mentioned for example vinylchloride, vinylidenechloride, allylchloride, chloroallylchloride, propargyl chloride, methallyl chloride, chloromethallyl chloride, pentenyl chloride, hexene dichloride, and octenyl chloride.

The reactivity of each of the halogen-substituted compounds exemplified above, varies depending on the conformation of a carbon atom to which a halogen atom is attached. For the reaction of the preferred production process of this invention, it is preferable to employ a compound which has one or more halogen atoms substituted at a primary or secondary carbon.

The reaction solvent used in the preferred production process of the present invention may be selected from aprotic polar solvents, including, for example, acetonitrile, dioxane, nitromethane, nitroethane, nitrobenzene, pyridine, dimethoxyethane, tetrahydrofuran, tetrahydropyran, 2-methyl-tetrahydrofuran, benzonitrile, N,N-dimethylformamide, N,N-dimethylacetamide, N,N-diethylformamide, dimethylsulfoxide, N-methylpyrrolidone, hexamethyl phosphoramide, sulforan, oxepane and glimes such as monoglime, diglime, triglime and tetraglime. Among the above solvents, acetonitrile, N,N-dimethylformamide, N,N-dimethylacetamide, dimethylsulfoxide, sulforan and tetraglime may be used as particularly preferable solvents. These solvents generally have strong miscibility with water and thus tend to induce mixing of water due to water absorption or upon recycling for re-use. Therefore, care must be exercised upon handling such solvents.

In a reaction system for carrying out the preferred production process of this invention, it is necessary that the reaction is initiated while at least a part of the strongly basic substance is suspended therein. In this state, water is present normally in an amount of 6% by weight or so in the reaction system. If the water content exceeds this figure, side reactions such as hydrolysis of a halogen-substituted compound or amide compound tend to occur easily, thereby considerably lowering the yield of an intended product. To make the reaction proceed efficiently and to increase the yield of an intended product, as will be appreciated from the above Examples 3 and 4 and Comparative Example 4, it is required to control the water content in the reaction system below at most 5% by weight, preferably, below 2.5% by weight, and more preferably, below 10,000 ppm.

There is no special limitation to the amount of solvent to be employed. However, it may account for 5–95% by weight, preferably, 10–90% by weight of the whole weight of the reactants including the solvent per se.

Next, the strongly basic substance to be employed in the preferred production process of the present invention is required to be a solid material and, when dissolved or suspended in water, to make the pH of the aqueous solution be at least 10, preferably, above 11. As such strongly basic substances, there are for example alkali metal hydroxides and alkaline earth metal hydroxides.

Specific examples of the above materials are as follows:

Among alkali metal hydroxides, may be mentioned for example sodium hydroxide, potassium hydroxide, lithium hydroxide, rubidium hydroxide, and cesium hydroxide. As alkaline earth metal hydroxides, may be mentioned for example beryllium hydroxide, magnesium hydroxide, calcium hydroxide, strontium hydroxide and barium hydroxide.

These strongly basic substances are generally subjected to their respective reactions in a solid form and the reactions are initiated while at least parts of the substances still remain in a suspended state.

In practising the preferred production process of this invention, the relative amounts of the raw materials, i.e. starting unsaturated amide compound, halogen-substituted compound and strongly basic substance, to be used vary depending on the reactivity between the halogen-substituted compound and starting unsaturated amide compound or depending on whether the intended product is an unsaturated N-monosubstituted amide compound or an unsaturated N,N-disubstituted amide compound, or for another reason. It is thus rather difficult to limit their relative amounts to specific ranges. However, generally speaking, where an unsaturated N-monosubstituted amide is intended, the halogen-substituted compound may be used in an amount of 0.2–10 moles, more preferably, 0.3–7 moles, per mole of the starting amide compound. On the other hand, the strongly basic substance may be used in an amount of 0.5–1.5 moles per mole of replaceable hydrogen of the starting amide compound as per the above Examples.

When the strongly basic substance is in excess amount, that is above 1.5 moles per mole of replaceable hydrogen, polymerization of the unsaturated compound and other side reactions will take place. On the other hand, when the amount used is below the 0.5 mole ratio amount the desired reaction fails to take place in a satisfactory manner.

When producing an N,N-disubstituted amide compound, the halogen-substituted compound may be used in an amount of 1.0–20 moles, more preferably 1.5–15 moles, per mole of the starting amide compound.

It is also possible to produce an unsaturated N,N-disubstituted amide compound having different substituent groups. Here, two halogen-substituted compounds of different types may be reacted simultaneously with the starting amide compound. The relative amounts of the two halogen-substituted compounds of different types vary depending on their reactivity. One of the halogen-substituted compounds may be used generally in an amount of 1.0–20 moles, preferably, 1.0–15 moles, per mole of the other halogen-substituted compound, the reactivity of the latter compound being supposed to be high. Also, as to a process for producing an unsaturated N,N-disubstituted amide compound whose substituent groups are different, it may be possible to react the starting amide compound with a first halogen-substituted compound to obtain an unsaturated N-monosubstituted amide compound and then to react the unsaturated N-monosubstituted amide compound with a second halogen-substituted compound. In the reaction system of the preferred production process of this invention it is preferable to incorporate a polymerization inhibitor to avoid the polymerization of raw materials and reaction product during the reaction step or purification step. The polymerization inhibitor is not necessarily to be limited to any specific one, but there may generally be mentioned phenol-type polymerization inhibitors, amine-type polymerization inhibitors, mercaptan-type polymerization inhibitors, and copper powder.

To carry out the reaction of the preferred production process of this invention, a conventional reaction tank may be used. However, where a strongly basic substance having low solubility is used, the basic substance may be packed in a column and a mixture solution of a starting amide compound and halogen-substituted compound may be recycled through the column. From the standpoint of the maintenance and control of the reaction facilities, it is more convenient to use a reaction tank.

When carrying out the reaction in a reaction tank, the raw materials may be charged in an arbitrary order. However, where a halogen-substituted compound having high reactivity is employed, it is convenient for the purpose of suppressing side reactions to add the halogen-substituted compound lastly so that it undergoes an intended reaction with the other two raw materials.

The reaction temperature of the preferred production process of this invention depends on the reactivity of a starting unsaturated amide compound and halogen-substituted compound to be used. However, a low reaction temperature tends to retard the proceeding of the reaction whereas a high reaction temperature induces side reactions such as hydrolysis of the unsaturated amide compounds and leads to a low yield. Accordingly, the reaction is usually carried out in a temperature range of $-20$ to $100°$ C., preferably $-10°$ to $70°$ C. Except for certain specific halogen-substituted compounds, the reaction temperature is more preferably in the range of $0°-50°$ C. As long as the reaction temperature is kept within the above temperature ranges, it is not always necessary to keep the temperature constant during the reaction. The reaction temperature may be suitably set while maintaining a full control on the progress of the reaction so as to allow the reaction to take place efficiently.

The reaction time varies, similar to the reaction temperature, depending on the types of starting amide compound and halogensubstituted compound to be used. It is however within 30 hours at the longest, and generally is within 10 hours. The progress of the reaction may be determined by watching the state of the reaction system or by checking the concentrations of the raw materials and intended product in the reaction system by virtue of gas chromatography or high-speed liquid chromatography.

Upon completion of the reaction, by-produced metal halide is filtered off in a known manner and, by subjecting the filtrate to a distillation under a reduced pressure, the intended product of high purity is obtained. However, when the metal halide is dissolved in the reaction solution or sublimable starting amide compound remains in the reaction solution, the solvent is distilled off from the reaction solution and the above substance is then removed with a mixed solvent, which forms two layers, such as benzenewater, chloroform-water or the like. Upon subjecting the organic layer to a distillation under a reduced pressure, the intended product can be obtained with high purity. Where the intended product has a high boiling point or tends to decompose by heat, it may be purified in accordance with a purification method such as solvent extraction or recrystallization.

Moreover, where the reaction solvent has great miscibility with water, such as dimethyl sulfoxide, and the intended product is highly hydrophobic such as an unsaturated N-alkylsubstituted amide compound, it is possible to add water to the reaction solution after the completion of the reaction and separate the intended product as an oil layer, or to extract the intended product with a solvent capable of forming two layers with water, such as benzene, toluene, or chloroform.

It is clear from the foregoing, that according to the preferred production process of this invention, it is possible to economically produce unsaturated N-substituted amide compounds which have an extremely wide variety of functions. Thus, unsaturated N-substituted amide compounds can be supplied to various application fields, to which conventional unsaturated N-substituted amide compounds could not be applied.

Since the preferred production process of the present invention is carried out with the same reaction pattern, it brings about an advantage that many types of unsaturated N-substituted amide compounds can be produced in the same reaction vessel, thereby making the process of this invention suitable for the production of many types of unsaturated N-substituted amide compounds in small quantities.

In short, according to the preferred production process of the present invention, an unsaturated N-substituted amide compound is produced with a high yield by initiating a reaction among a starting amide compound such as an unsaturated aliphatic mono or dicarboxylic acid amide, a halogen-substituted compound such as an alkyl halide, alkyl polyhalide, aralkylhalide or alkenyl halide, and a strongly basic substance while maintaining the basic substance in a suspended state, in conjunction with the above stated preferred production process requirements.

What is claimed is:

1. In a process for producing an unsaturated N-substituted amide compound by bringing a strongly basic substance, a starting amide compound and a halogen-substituted compound into simultaneous contact in an aprotic polar solvent to react them together, the improvement wherein the reaction system the starting amide compound is acrylamide or methacrylamide; the strongly basic substance is an alkali metal hydroxide; the halogen-substituted compound is an allyl halide alkyl polyhalide, aralkyl halide or allyl halide compound; the amount of the strongly basic substance is 0.5-1.5 moles per mole of replaceable hydrogen of the starting amide compound; the amount of aprotic polar solvent is 10-90% by weight of the whole weight of the reactants including the solvent per se; the amount of water present at the beginning of the reaction is 5% by weight or less of the reaction system; and the reaction is initiated while maintaining the basic substance in a suspended state.

* * * * *

UNITED STATES PATENT AND TRADEMARK OFFICE
CERTIFICATE OF CORRECTION

PATENT NO. : 4,835,312

DATED : May 30, 1989

INVENTOR(S) : Itoh et al.

It is certified that error appears in the above-identified patent and that said Letters Patent is hereby corrected as shown below:

On the first page of the patent document, at [73], Assignee data, change the Assignee from "Mitsui Chemicals, Incorporated" to --Mitsui Toatsu Chemicals, Incorporated--.

Signed and Sealed this

Sixteenth Day of January, 1990

Attest:

JEFFREY M. SAMUELS

Attesting Officer     Acting Commissioner of Patents and Trademarks